US008376736B2

(12) United States Patent
Simpson et al.

(10) Patent No.: US 8,376,736 B2
(45) Date of Patent: Feb. 19, 2013

(54) CARBON CAPTURE IN FERMENTATION

(75) Inventors: Sean Dennis Simpson, Auckland (NZ);
Christophe Collet, Auckland (NZ);
Richard Llewellyn Sydney Forster,
Pukekohe (NZ); **Michael Charles
Milner Cockrem**, Madison, WI (US);
Simon David Oakley, Auckland (NZ)

(73) Assignee: LanzaTech New Zealand Limited,
Auckland (NZ)

( * ) Notice: Subject to any disclaimer, the term of this patent is extended or adjusted under 35 U.S.C. 154(b) by 36 days.

(21) Appl. No.: 12/739,424

(22) PCT Filed: Oct. 23, 2008

(86) PCT No.: PCT/NZ2008/000275
§ 371 (c)(1),
(2), (4) Date: Aug. 10, 2010

(87) PCT Pub. No.: WO2009/058028
PCT Pub. Date: May 7, 2009

(65) Prior Publication Data
US 2010/0317074 A1 Dec. 16, 2010

Related U.S. Application Data

(60) Provisional application No. 60/983,199, filed on Oct. 28, 2007, provisional application No. 60/983,203, filed on Oct. 28, 2007, provisional application No. 60/987,581, filed on Nov. 13, 2007.

(30) Foreign Application Priority Data

Oct. 28, 2007 (NZ) ........................................ 560757

(51) Int. Cl.
*C12P 7/00* (2006.01)
*C12P 7/54* (2006.01)

(52) U.S. Cl. ........................................ 432/132; 435/140
(58) Field of Classification Search .................. 435/132, 435/140
See application file for complete search history.

(56) References Cited

U.S. PATENT DOCUMENTS

| 4,021,579 | A | | 5/1977 | Barrett |
|---|---|---|---|---|
| 5,100,553 | A | | 3/1992 | Nomura et al. |
| 5,173,429 | A | | 12/1992 | Gaddy et al. |
| 5,593,886 | A | | 1/1997 | Gaddy |
| 5,807,722 | A | | 9/1998 | Gaddy |
| 5,821,111 | A | * | 10/1998 | Grady et al. ............... 435/252.5 |
| 5,861,137 | A | | 1/1999 | Edlund |
| 6,136,577 | A | | 10/2000 | Gaddy |
| 6,340,581 | B1 | | 1/2002 | Gaddy |
| 6,368,819 | B1 | | 4/2002 | Gaddy et al. |
| 6,425,401 | B1 | | 7/2002 | Williams |
| 6,605,376 | B2 | | 8/2003 | Verykios |
| 6,737,257 | B2 | | 5/2004 | Blum |
| 6,753,170 | B2 | | 6/2004 | Gaddy et al. |
| RE39,175 | E | | 7/2006 | Gaddy et al. |
| 7,078,201 | B2 | | 7/2006 | Burmaster |
| 7,097,762 | B1 | * | 8/2006 | Ruocco et al. ............... 210/104 |
| 7,196,218 | B2 | | 3/2007 | Gaddy et al. |
| 7,285,402 | B2 | | 10/2007 | Gaddy et al. |
| 8,026,095 | B2 | * | 9/2011 | Krieg ........................... 435/298.1 |
| 2003/0211585 | A1 | * | 11/2003 | Gaddy et al. ................. 435/161 |
| 2005/0266540 | A1 | | 12/2005 | Offerman et al. |
| 2006/0252137 | A1 | | 11/2006 | Burmaster |
| 2007/0049648 | A1 | * | 3/2007 | Shessel ........................ 518/702 |
| 2007/0275447 | A1 | * | 11/2007 | Lewis et al. .................. 435/161 |
| 2007/0298478 | A1 | | 12/2007 | Offerman et al. |

FOREIGN PATENT DOCUMENTS

| CN | 1433718 | 1/2003 |
|---|---|---|
| CN | 1433718 | 8/2003 |
| DE | 4230644 | 3/1994 |
| EP | 0041702 | 12/1981 |
| EP | 0 085 757 | 11/1982 |
| EP | 0085757 A1 | 8/1983 |
| EP | 0085757 B1 | 2/1986 |
| EP | 1 303 629 | 7/2001 |
| EP | 1 303 629 | 7/2006 |
| JP | 61-205478 | 9/1986 |
| JP | 62-091293 | 4/1987 |
| JP | 62-91293 | 4/1987 |
| JP | 2-312584 | 12/1990 |
| JP | 4-171021 | 6/1992 |
| JP | 4-1820828 | 6/1992 |
| JP | 4171021 | 6/1992 |
| JP | 4180828 | 6/1992 |
| JP | 2002-312584 | 10/2002 |
| JP | 2003-135088 | 5/2003 |
| JP | 2005-328849 | 12/2005 |
| JP | 2005328849 | 12/2005 |
| NZ | 546496 | 4/2006 |
| WO | 02/08438 | 1/2002 |
| WO | WO 02/08438 | 1/2002 |
| WO | WO03/094598 | 11/2003 |

(Continued)

OTHER PUBLICATIONS

Wang et al. (Elucidation of Growth inhibition and Acetic Acid Production by *Clostridium thermoaceticum*. Appl. Environ. Microbiol. 1984 47(2):294-298).*

Phillips, John R. et al. "Synthesis Gas as Substrate for the Biological Production of Fuels and Chemicals." Applied Biochemistry and Biotechnology. vol. 45/46, 1994, pp. 145-157.

Ragsdale, Stephen W. "Life with Carbon Monoxide". Critical Reviews in Biochemistry and Molecular Biology, vol. 39, 2004, pp. 165-195.

(Continued)

*Primary Examiner* — Karen Cochrane Carlson
*Assistant Examiner* — Natalie Moss
(74) *Attorney, Agent, or Firm* — Frank S. Molinaro

(57) ABSTRACT

The invention relates to methods of capturing carbon by microbial fermentation of a gaseous substrate comprising CO. The methods of the invention include converting CO to one or more products including alcohols and/or acids and optionally capturing CO2 to improve overall carbon capture. In certain aspects, the invention relates to processes for producing alcohols, particularly ethanol, from industrial waste streams, particularly steel mill off-gas.

7 Claims, 9 Drawing Sheets

FOREIGN PATENT DOCUMENTS

| WO | 2005/118826 | 12/2005 |
| WO | WO 2005/118826 | 12/2005 |
| WO | 2006/108532 | 10/2006 |
| WO | WO 2006/108532 | 10/2006 |
| WO | 2007/064545 | 6/2007 |
| WO | WO 2007/064545 | 6/2007 |
| WO | 2007/117157 | 10/2007 |
| WO | WO 2007/117157 | 10/2007 |
| WO | WO 2007/117157 A1 * | 10/2007 |
| WO | 2008/028055 | 3/2008 |
| WO | WO 2008/028055 | 3/2008 |
| WO | 2008/115080 | 9/2008 |
| WO | WO 2008/115080 | 9/2008 |
| WO | 2008/154301 | 12/2008 |
| WO | WO 2008/154301 | 12/2008 |
| WO | 2009/020747 | 2/2009 |
| WO | WO 2009/020747 | 2/2009 |
| WO | WO2009064201 | 5/2009 |

OTHER PUBLICATIONS

Henstra, Anne M, et al. "Microbiology of synthesis gas fermentation for biofuel production." Current Opinion in Biotechnology, vol. 18, 2007, pp. 200-206.

Abrini, Jamal et al. "*Clostridium autoethanogenum*, sp. nov., an anaerobic bacterium that produces ethanol from carbon monoxide." Archives of Microbiology, vol. 161, 1994, pp. 345-351.

Phillips et al. "Synthesis gas as substrate for the biological production of fuels and chemicals." 1994, Applied biochemistry and biotechnology, 45(1), pp. 145-157.

Abrini et al. "*Clostrdium autoethanogenum*, sp. Noc., an anaerobic bacterium that produces ethanol from carbon monoxide." Archives of Microbiology, 1994, 161(4), pp. 345-351.

Ragsdale, Stephen W. "Life with Carbon Monoxide." Critical reviews in biochemistry and molecular biology, 2004, 39(3), pp. 165-195.

Henstra et al. "Microbiology of synthesis gas fermentation for biofuel production." Current opinion in biotechnology, 2007, 18(3) pp. 200-206.

Najafpour G et al, ethanol and acetate synthesis from waste gas using batch culture of *Clostridium* Ljungdahlii, Enzyme and Microbial Technology, Stoneham MA, US.

Non-Final Office Action in U.S. Appl. No. 12/821,468, dated Feb. 4, 2011, 23 pages.

Final Office Action in U.S. Appl. No. 12/821,468, dated Jul. 14, 2011, 23 pages.

* cited by examiner

CARBON CAPTURE IN FERMENTATION

CROSS REFERENCE TO RELATED APPLICATIONS

This application is a National Stage of International Application No. PCT/NZ2008/000275, filed Oct. 23, 2008, which claims the priority of New Zealand Application No. 560757 filed Oct. 28, 2007, U.S. Provisional Application No. 60/983,199, filed Oct. 28, 2007, U.S. Provisional Application No. 60/983,203, filed Oct. 28, 2007, U.S. Provisional Application No. 60/987,581, filed Nov. 13, 2007.

FIELD OF THE INVENTION

This invention relates to systems and methods for improving overall carbon capture and/or improving overall efficiency in processes including microbial fermentation. In particular, the invention relates to improving carbon capture and/or improving efficiency in processes including microbial fermentation of a substrate comprising CO derived from an industrial source.

BACKGROUND OF THE INVENTION

Ethanol is rapidly becoming a major hydrogen-rich liquid transport fuel around the world. Worldwide consumption of ethanol in 2005 was an estimated 12.2 billion gallons. The global market for the fuel ethanol industry has also been predicted to grow sharply in future, due to an increased interest in ethanol in Europe, Japan, the USA, and several developing nations.

For example, in the USA, ethanol is used to produce E10, a 10% mixture of ethanol in gasoline. In E10 blends the ethanol component acts as an oxygenating agent, improving the efficiency of combustion and reducing the production of air pollutants. In Brazil, ethanol satisfies approximately 30% of the transport fuel demand, as both an oxygenating agent blended in gasoline, and as a pure fuel in its own right. Also, in Europe, environmental concerns surrounding the consequences of Green House Gas (GHG) emissions have been the stimulus for the European Union (EU) to set member nations a mandated target for the consumption of sustainable transport fuels such as biomass derived ethanol.

The vast majority of fuel ethanol is produced via traditional yeast-based fermentation processes that use crop derived carbohydrates, such as sucrose extracted from sugarcane or starch extracted from grain crops, as the main carbon source. However, the cost of these carbohydrate feed stocks is influenced by their value as human food or animal feed, while the cultivation of starch or sucrose-producing crops for ethanol production is not economically sustainable in all geographies. Therefore, it is of interest to develop technologies to convert lower cost and/or more abundant carbon resources into fuel ethanol.

CO is a major, free, energy-rich by-product of the incomplete combustion of organic materials such as coal or oil and oil derived products. For example, the steel industry in Australia is reported to produce and release into the atmosphere over 500,000 tonnes of CO annually.

Catalytic processes may be used to convert gases consisting primarily of CO and/or CO and hydrogen (H2) into a variety of fuels and chemicals. Micro-organisms may also be used to convert these gases into fuels and chemicals. These biological processes, although generally slower than chemical reactions, have several advantages over catalytic processes, including higher specificity, higher yields, lower energy costs and greater resistance to poisoning.

The ability of micro-organisms to grow on CO as a sole carbon source was first discovered in 1903. This was later determined to be a property of organisms that use the acetyl coenzyme A (acetyl CoA) biochemical pathway of autotrophic growth (also known as the Woods-Ljungdahl pathway and the carbon monoxide dehydrogenase/acetyl CoA synthase (CODH/ACS) pathway). A large number of anaerobic organisms including carboxydotrophic, photosynthetic, methanogenic and acetogenic organisms have been shown to metabolize CO to various end products, namely CO2, H2, methane, n-butanol, acetate and ethanol. While using CO as the sole carbon source, all such organisms produce at least two of these end products.

Anaerobic bacteria, such as those from the genus *Clostridium*, have been demonstrated to produce ethanol from CO, CO2 and H2 via the acetyl CoA biochemical pathway. For example, various strains of *Clostridium ljungdahlii* that produce ethanol from gases are described in WO 00/68407, EP 117309, U.S. Pat. Nos. 5,173,429, 5,593,886, and 6,368,819, WO 98/00558 and WO 02/08438. The bacterium *Clostridium autoethanogenum* sp is also known to produce ethanol from gases (Abrini et al., Archives of Microbiology 161, pp 345-351 (1994)).

However, ethanol production by micro-organisms by fermentation of gases is always associated with co-production of acetate and/or acetic acid. As some of the available carbon is converted into acetate/acetic acid rather than ethanol, the efficiency of production of ethanol using such fermentation processes may be less than desirable. Also, unless the acetate/acetic acid by-product can be used for some other purpose, it may pose a waste disposal problem. Acetate/acetic acid is converted to methane by micro-organisms and therefore has the potential to contribute to GHG emissions.

Microbial fermentation of CO in the presence of H2 can lead to substantially complete carbon transfer into an alcohol. However, in the absence of sufficient H2, some of the CO is converted into alcohol, while a significant portion is converted to CO2 as shown in the following equations:

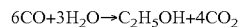

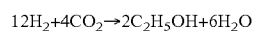

The production of $CO_2$ represents inefficiency in overall carbon capture and if released, also has the potential to contribute to Green House Gas emissions.

WO2007/117157, the disclosure of which is incorporated herein by reference, describes a process that produces alcohols, particularly ethanol, by anaerobic fermentation of gases containing carbon monoxide. Acetate produced as a by-product of the fermentation process is converted into hydrogen gas and carbon dioxide gas, either or both of which may be used in the anaerobic fermentation process. WO2008/115080, the disclosure of which is incorporated herein by reference, describes a process for the production of alcohol(s) in multiple fermentation stages. By-products produced as a result of anaerobic fermentation of gas(es) in a first bioreactor can be used to produce products in a second bioreactor. Furthermore, by-products of the second fermentation stage can be recycled to the first bioreactor to produce products.

U.S. Pat. No. 7,078,201 and WO 02/08438 also describe improving fermentation processes for producing ethanol by varying conditions (e.g. pH and redox potential) of the liquid nutrient medium in which the fermentation is performed. As disclosed in those publications, similar processes may be used to produce other alcohols, such as butanol.

Even minor improvements to a fermentation process for producing one or more acids and/or one or more alcohols can have a significant impact on the efficiency, and more particularly, the commercial viability, of such a process.

For example, regardless of the source used to feed the fermentation reaction, problems can occur when there are breaks in the feed supply. More particularly, such interruptions can be detrimental to the efficiency of production by the micro-organisms used in the reaction, and in some cases, can be harmful thereto. For example, where CO gas in an industrial waste gas stream may be used in fermentation reactions to produce acids/alcohols, there may be times when the stream is not produced. During such times, the micro-organisms used in the reaction may go into an inactive, non-productive state or hibernation. When the stream is available again, there may then be a lag before the micro-organisms are fully productive at performing the desired reaction. Accordingly, there would be significant benefit if there were a means to reduce or eliminate this lag time.

As another example, in many industrial processes, scrubber systems or apparatus are used to reduce the concentration of particulates (such as dust) and other components that contaminate exhaust gases. Dry or wet scrubbing systems are known. In a wet scrubbing system, water or other liquids are used to "scrub" the contaminants from the gas stream. A typical wet scrubbing system is seen in steel mills, where water is used to clean flue gases generated at various stages of steel manufacture: for example gases generated by the coking ovens, the blast furnace, the basic oxygen furnace or the electric arc furnace. While scrubbing has the benefit of reducing the level of contaminants within exhaust gases, it by no means eliminates the contaminants altogether. The unwanted substances are simply removed from the gas into a solid or powder form or into the scrubber water or liquid. The water or liquid used in the scrubber system thus becomes a waste stream generated by this industry. The disposal of such waste represents an environmental hazard. The need to clean and dispose of such waste materials also represents a significant cost to the industry.

While conventional industrial scrubbers (such as at steel mills) remove a portion of the contaminants from industrial waste gas streams, it has been accepted in the art that additional scrubbing and/or treatment steps are required to be performed on the gases before they may be used to feed a fermentation reaction due to the perceived harmful effects of such gases on the micro-organisms used in the reaction. See, for example, Datar et al., Fermentation of biomass-generated producer gas to ethanol, 2004, Biotechnology and Bioengineering Vol. 86, pp 587-594. The use of additional scrubbing and/or treatment steps requires additional space in an industrial plant, which can be particularly problematic where the use of fermentation processes is added to an existing plant. Accordingly, there is a need for improved processes in which such additional scrubbing or other treatment steps are not required or are at least kept to minimum.

It is an object of the present invention to provide system(s) and/or method(s) that overcomes or ameliorates at least one disadvantage known in the art and provides the public with new methods for improved and/or increased production of a variety of useful products.

SUMMARY OF THE INVENTION

In a first aspect, there is provided a method of capturing carbon by microbial fermentation, the method comprising:
  i. receiving off or waste gas stream(s) comprising CO from an industrial process;
  ii. passing the gas stream(s) to a bioreactor containing a culture of one or more microorganisms; and
  iii. fermenting the culture in the bioreactor to produce one or more products.

In some embodiments, the method comprises capturing at least a portion of a CO2 content, using a CO2 remover, from one or both of:
  i. a stream prior to the stream entering the bioreactor; and
  ii. a stream after the stream has exited the bioreactor.

In certain embodiments, the method comprises a first gas separation step, the first gas separation step comprising (i) receiving a gas stream; (ii) substantially separating at least one portion of the gas stream, wherein the portion comprises one or more components of the gas stream; and (iii) passing at least part of the separated portion(s) to the bioreactor. In one embodiment, the at least part of the separated portion(s) passed to the bioreactor comprises CO.

In particular embodiments, the method comprises a second gas separation step, the second gas separation step comprising (i) receiving a gas stream; (ii) substantially separating at least one portion of the gas stream, wherein the portion comprises one or more components of the gas stream; and (iii) passing at least part of the separated portion(s) to the CO2 remover. In one embodiment, the gas separation step substantially separates CO2 from the gas stream and passes the separated CO2 to the CO2 remover.

In particular embodiments, the method comprises buffering of a gas stream and passing at least a portion thereof to the bioreactor in a substantially continuous manner. In one embodiment, the step of buffering comprises (i) receiving an intermittent or non-continuous gas stream at storage means; and (ii) passing a substantially continuous stream to the bioreactor from the storage means.

In certain embodiments, the method comprises blending one or more gas streams with at least one other stream.

In certain embodiments, the method comprises adding scrubber water from an industrial process to the bioreactor.

In a second aspect, there is provided a system for capturing carbon by microbial fermentation, the system comprising an inlet for receiving off or waste gas from an industrial process, wherein, in use, the system is configured to pass at least a portion of the gas to a bioreactor to generate products by microbial fermentation.

In some embodiments, the system comprises a CO2 remover configured to, in use, capture at least a portion of a CO2 content from one or both of:
  i. a stream prior to the stream entering the bioreactor; and
  ii. a stream after the stream has exited the bioreactor.

In particular embodiments, the system comprises a first gas separator configured to in use: (i) receive a gas stream; (ii) substantially separate at least one portion of the gas stream, wherein the portion comprises one or more components of the gas stream; (iii) pass at least part of the separated portion to the bioreactor. In one embodiment, the first gas separator is adapted to, in use, substantially separate CO from the gas stream and pass the separated CO to the bioreactor.

In particular embodiments, the system comprises a second gas separator configured to in use: (i) receive a gas stream; (ii) substantially separate at least one portion of the gas stream, wherein the portion comprises one or more components of the gas stream; and (iii) pass at least part of the separated portion to the CO2 remover. In one embodiment, the second gas separator is adapted to separate CO2 from the gas stream and pass the separated CO2 to the CO2 remover.

In some embodiments, the system comprises buffering means adapted to, in use, provide a substrate stream to the bioreactor in a substantially continuous stream. In particular embodiments, the buffering means comprises a buffer storage tank adapted to in use:
  i. receive an intermittent or non-continuous gas/substrate stream; and
  ii. pass a substantially continuous gas/substrate stream to the bioreactor.

In certain embodiments, the system comprises blending means adapted to, in use, combine a gas stream with at least one other stream prior to passing the combined stream to the bioreactor.

In particular embodiments, the system comprises at least one determining means to monitor the composition of at least one gas stream fed to and/or exhausted from the bioreactor. In certain embodiments, the system comprises control means for directing at least a portion of one or more gas/exhaust stream(s) to one or more of:
 i. the bioreactor;
 ii. the CO2 remover;
 iii. the first gas separator;
 iv. the second gas separator;
 v. the buffering means;
 vi. the blending means; and
 vii. an exhaust means,
the particular one(s) of destinations i to vii being selected at least in part based on the determination made by the determining means.

In a third aspect, there is provided a system for increasing overall carbon capture in a process of producing products in a bioreactor by microbial fermentation of a substrate, the system including a CO2 remover configured to capture at least a portion of a CO2 content from one or both of:
 i. a stream prior to the stream entering the bioreactor; and
 ii. a stream after the stream has exited the bioreactor.

In a fourth aspect, there is provided a system for increasing the efficiency of processes for producing products by microbial fermentation of gas(es) wherein supply of said gas(es) is intermittent, the system comprising buffering means adapted to receive and store at least a portion of the gas, and a bioreactor adapted to receive at least a portion of the gas from the buffering means.

In a fifth aspect, there is provided a system for increasing the efficiency of processes for producing products by microbial fermentation of gas(es), the system comprising a gas separator configured to receive a gas stream and to pass at least a portion of said stream to a bioreactor.

In a sixth aspect, there is provided a steel mill adapted to produce alcohols by microbial fermentation of waste gas(es).

According to particular aspects, the systems and methods of the invention are adapted for use in a process of producing alcohols, more particularly ethanol and/or butanol, by anaerobic fermentation of gases containing carbon monoxide. Additionally or alternatively, acids, such as acetic acid or acetate, may be produced. However, the invention is not limited thereto and is intended to cover other fermentation reactions, including aerobic fermentations, those generating different products, such as isopropanol or $H_2$, and those not including fermentation of carbon containing gases.

Embodiments of the invention find particular application in the fermentation of a gaseous substrate comprising CO to produce acids and/or alcohols although particular aspects of the invention are not limited to substrates including CO. The gaseous substrate may comprise a gas obtained as a by-product of an industrial process. In certain embodiments, the industrial process is selected from the group consisting of ferrous metal products manufacturing, non-ferrous products manufacturing, petroleum refining processes, gasification of biomass, gasification of coal, electric power production, carbon black production, ammonia production, methanol production and coke manufacturing. Most preferably, the gaseous substrate comprises a gas obtained from a steel mill.

In certain preferred embodiments the gaseous substrate comprises from 20% CO to 100% CO by volume, such as from 50% CO to 95% CO by volume, such as from 50% to 70% CO by volume. Gaseous substrates having lower concentrations of CO, such as 6%, may also be appropriate, particularly when $H_2$ and $CO_2$ are also present.

In preferred embodiments, the fermentation reaction is carried out by one of more strains of carboxydotrophic bacteria.

Preferably, the carboxydotrophic bacterium is selected from *Clostridium, Moorella* and *Carboxydothermus*. Most preferably, the carboxydotrophic bacterium is *Clostridium autoethanogenum*.

BRIEF DESCRIPTION OF THE DRAWINGS

The invention will now be described in detail with reference to the accompanying Figures in which.

DETAILED DESCRIPTION OF THE INVENTION

Figure 1:
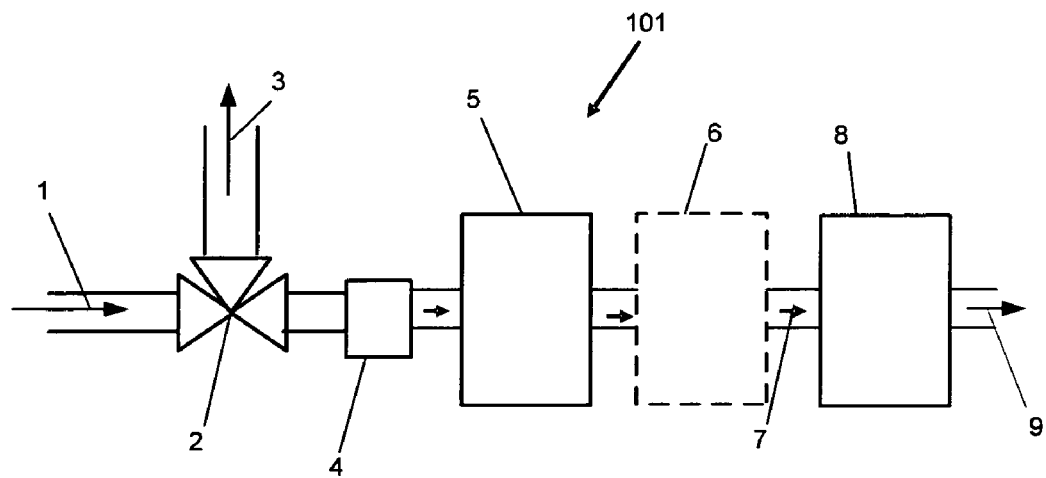
FIG. 1: is a schematic representation of a system including a CO2 remover downstream of a bioreactor according to certain embodiments of the invention.

In accordance with certain methods of the invention, waste or off gases from an industrial process may be used to supplement and/or support fermentation reactions with minimal additional processing or treatment steps on the gases prior to passing them to the bioreactor in which the fermentation process is performed. This is particularly surprising, because it is commonly believed that the waste or off gases contain contaminants that would be detrimental to the growth and/or survival of the micro-organisms used in the fermentation. The invention has particular applicability to waste or off gases produced during steel making processes, particularly those containing CO, which are used to produce alcohols (e.g. ethanol, butanol, isopropanol) and/or acids (e.g. butyric acid, acetic acid and/or acetate) and/or hydrogen. While there are a variety of different micro-organisms capable of performing such processes, the invention has particular applicability to fermentation processes involving the use of *Clostridium autoethanogenum*.

This aspect of the invention has significant value in that it reduces the number of or eliminates the pre-processing steps performed on waste gases prior to their use in a fermentation reaction. Thus, the invention provides for wider suitability and/or applicability of such fermentation processes, particularly in established industrial plants where a limited, predetermined amount of space may be available for adding equipment to perform fermentations. Also, because no or limited scrubbing and/or pre-treatment processes are performed on the waste gases, embodiments of the invention may also ameliorate or reduce waste from industrial processes due to there being no need to process the waste or contaminants resulting from the scrubbing and/or pre-treatment processes.

Waste gases from industrial processes other than steel manufacturing may be used in a similar fashion in the methods of the invention. The invention is readily applicable to fermentation reactions that utilise gaseous substrates other than carbon monoxide as a source of carbon and energy, produce alcohols other than ethanol, produce hydrogen, and/or which utilise micro-organisms other than *Clostridium autoethanogenum*.

Substrates suitable for use in fermentation processes often also contain CO2. In addition, in many fermentation reactions, for example where CO is converted to products including acids and/or alcohols, significant volumes of CO2 can be produced. The present invention relates to methods, systems, and processes to improve the overall carbon capture in such fermentation reactions.

In accordance with methods of the invention, the removal of CO2 (or other gases) from a substrate stream will increase the CO concentration (or CO partial pressure in a gaseous substrate) and so increase the efficiency of fermentation reactions where CO is a substrate. Increasing CO partial pressure in a gaseous substrate increases CO mass transfer into a fermentation media. Furthermore, the composition of gas streams used to feed a fermentation reaction can have a significant impact on the efficiency and/or costs of that reaction. For example, O2 may reduce the efficiency of an anaerobic fermentation process. In addition, processing of unwanted or unnecessary gases in stages of a fermentation process before or after fermentation can increase the burden on such stage (e.g. where the gas stream is compressed before entering a bioreactor, unnecessary energy may be used to compress gases that are not needed in the fermentation). Additionally or alternatively, the CO2 component of a particular substrate stream may be of greater value if used in another reaction, including another fermentation reaction.

Furthermore, in accordance with methods of the invention, increasing the concentration of CO2 in a stream, for example increasing CO2 partial pressure in a gaseous stream, will increase the efficiency of processes that utilise CO2, such as fermentation. Examples of processes that utilise CO2, such as fermentations, are well known in the art. Examples of some such processes are described in detail in WO2006/108532 and are incorporated herein by reference.

Certain aspects of the invention generally relate to systems and methods for improving overall carbon capture in processes including microbial fermentation. In particular embodiments, the invention relates to the capture of CO2 from substrate streams provided to a fermentation reaction. Alternatively, or in addition, the invention relates to the capture of CO2 from exhaust streams after the stream has exited the bioreactor. In particular embodiments of the invention, the substrate provided to the fermentation reaction comprises CO.

Furthermore, it may be desirable to remove and/or capture carbon containing components such as CO2 and/or $CH_4$ to improve overall carbon capture of the process as described above. Additionally or alternatively, components of a particular gas may be of greater value if used elsewhere than in the fermentation reaction (e.g. H2 is of considerable value for use as a fuel).

Certain aspects of the invention generally relate to systems and methods for improving the efficiency of processes of producing products by microbial fermentation of gases, particularly through use of at least one gas separation process of the gas stream used to feed the fermentation and/or the gas stream produced as a result of the fermentation. In one embodiment, a gas separator is configured to substantially separate at least one portion of the gas stream, wherein the portion comprises one or more components. For example, the gas separator may separate CO2 from a gas stream comprising the following components: CO, CO2, H2, wherein the CO2 may be passed to a CO2 remover and the remainder of the gas stream (comprising CO and H2) may be passed to a bioreactor.

The gas streams generated during industrial processes, such as batch processing of steel from iron in a steel mill, can be intermittent in nature, which may not be desirable when such gases are used for bio-conversion. In addition, the nature of the streams may be such that the gas composition varies in a cyclic nature during various phases of a particular industrial process. For example, in the steel making process, during periods when essentially oxygen free gases are generated, concentrations of CO are highest. Conversely, when the gases are largely CO free, significant levels of O2 may be present. Many fermentation reactions require high CO concentrations that are essentially free of O2, such as those involving anaerobic bacteria, particularly, carboxydotrophic bacteria.

Certain aspects of the invention generally relate to systems and methods for improving the efficiency of processes for producing products by microbial fermentation of gases where the gas streams (or other sources such as dissolved gases and/or carbohydrates) used to feed the fermentation reaction are intermittent in nature. Particular embodiments of the invention are described in the context of the steel making industry, with carboxydotrophic bacteria being used to produce acids and/or alcohols, particularly ethanol or butanol. Those skilled in the art will be aware, upon consideration of the instant disclosure, that the invention may be applied to different industries, as well as to various stages in the steel making process. Also, those skilled in the art will be aware, upon consideration of the instant disclosure, that the invention may be applied to other fermentation reactions, including those using the same or different micro-organisms. It is therefore intended that the scope of the invention is not limited to the particular embodiments and/or applications described but is instead to be understood to relate to any fermentation process in which at least one element used to feed the process is supplied in an intermittent manner, such as where waste gases from an industrial process are used, the gases being produced in an intermittent manner.

Certain aspects of the invention generally relate to systems and methods for improving the efficiency of processes for producing products and/or capturing carbon by microbial fermentation of substrate streams wherein the substrate streams are blended with additional streams to optimise the composition for microbial fermentation.

Surprisingly, when scrubber water from the basic oxygen steel making process or basic oxygen furnace off-gas stream from a steel mill is mixed with a standard microbial growth media in a fermentation reaction utilising gas containing carbon monoxide to produce ethanol in accordance with methods of the invention, growth of *Clostridium autoethanogenum*, as well as its ability to produce ethanol, is improved. This is particularly surprising, as the water was expected to contain contaminants that would be detrimental to the growth and survival of micro-organisms.

This finding has significant value in ameliorating or reducing waste from industrial processes, increasing the efficiency of fermentation reactions, reducing the level of media required to support fermentation reactions, and accordingly lowering operating costs. The invention can thus serve to decrease the level of acetate by-product formed during such fermentation reactions. This can be of benefit in situations where the acetate is not of use and would otherwise be discarded, increasing costs to the industry and posing an environmental problem.

Based on the results obtained, the invention enables the use of scrubber water as a primary feedstock for fermentation reactions. The scrubber water from industrial processes other than steel manufacturing may be used in a similar fashion. In addition, the invention is readily applicable to fermentation reactions which utilise gaseous substrates other than carbon monoxide as a source of carbon and energy, produce alcohols other than ethanol, produce hydrogen, and/or which utilise micro-organisms other than *Clostridium autoethanogenum*.

One or more features of each of any two or more of the aforementioned aspects may be combined and used within the same system with the attendant advantages thereof.

DEFINITIONS

Unless otherwise defined, the following terms as used throughout this specification, are defined as follows:

The term "carbon capture" as used herein refers to the sequestration of carbon compounds including $CO_2$ and/or CO from a stream comprising $CO_2$ and/or CO and either:
converting the $CO_2$ and/or CO into products; or
converting the $CO_2$ and/or CO into substances suitable for long term storage; or
trapping the $CO_2$ and/or CO in substances suitable for long term storage;
or a combination of these processes.

The term "substrate comprising carbon monoxide" and like terms should be understood to include any substrate in which carbon monoxide is available to one or more strains of bacteria for growth and/or fermentation, for example.

"Gaseous substrates comprising carbon monoxide" include any gas which contains carbon monoxide. The gaseous substrate will typically contain a significant proportion of CO, preferably at least about 5% to about 100% CO by volume.

The term "bioreactor" includes a fermentation device consisting of one or more vessels and/or towers or piping arrangements, which includes the Continuous Stirred Tank Reactor (CSTR), Immobilized Cell Reactor (ICR), Trickle Bed Reactor (TBR), Bubble Column, Gas Lift Fermenter, Membrane Reactor such as Hollow Fibre Membrane Bioreactor (HFMBR), Static Mixer, or other vessel or other device suitable for gas-liquid contact.

The term "co-substrate" refers to a substance that, while not necessarily being the primary energy and material source for product synthesis, can be utilised for product synthesis when added to another substrate, such as the primary substrate.

The term "acid" as used herein includes both carboxylic acids and the associated carboxylate anion, such as the mixture of free acetic acid and acetate present in a fermentation broth as described herein. The ratio of molecular acid to carboxylate in the fermentation broth is dependent upon the pH of the system. In addition, the term "acetate" includes both acetate salt alone and a mixture of molecular or free acetic acid and acetate salt, such as the mixture of acetate salt and free acetic acid present in a fermentation broth as described herein.

The term "limiting concentration" means an initial concentration of a given component in a microbial fermentation medium that is sufficiently low to ensure that it will be depleted at some stage in the fermentation.

The term "intermittent stream" means not only streams which are not continuously available, but also streams which do not continuously have a desired composition.

The term "scrubber water" refers to water or other liquids resulting from the cleaning of gas streams generated during industrial processes such as ferrous metal products manufacturing, non-ferrous products manufacturing, petroleum refining processes, gasification of coal, gasification of biomass, electric power production, carbon black production, and coke manufacturing.

The term "directly", as used in relation to the passing of industrial off or waste gases to a bioreactor, is used to mean that no or minimal processing or treatment steps, such as cooling and particulate removal are performed on the gases prior to them entering the bioreactor (note: an oxygen removal step may be required for anaerobic fermentation).

The term "desired composition" is used to refer to the desired level and types of components in a substance, such as, for example, of a gas stream. More particularly, a gas is considered to have a "desired composition" if it contains a particular component (e.g. CO and/or $CO_2$) and/or contains a particular component at a particular level and/or does not contain a particular component (e.g. a contaminant harmful to the micro-organisms) and/or does not contain a particular component at a particular level. More than one component may be considered when determining whether a gas stream has a desired composition.

The term "stream" is used to refer to a flow of material into, through and away from one or more stages of a process, for example, the material that is fed to a bioreactor and/or an optional $CO_2$ remover. The composition of the stream may vary as it passes through particular stages. For example, as a stream passes through the bioreactor, the CO content of the stream may decrease, while the $CO_2$ content may increase. Similarly, as the stream passes through the $CO_2$ remover stage, the $CO_2$ content will decrease.

Unless the context requires otherwise, the phrases "fermenting", "fermentation process" or "fermentation reaction" and the like, as used herein, are intended to encompass both the growth phase and product biosynthesis phase of the process.

The terms "increasing the efficiency", "increased efficiency" and the like, when used in relation to a fermentation process, include, but are not limited to, increasing one or more of: the rate of growth of micro-organisms in the fermentation, the volume or mass of desired product (such as alcohols) produced per volume or mass of substrate (such as carbon monoxide) consumed, the rate of production or level of production of the desired product, and the relative proportion of the desired product produced compared with other by-products of the fermentation, and further may reflect the value (which may be positive or negative) of any by-products generated during the process.

In one aspect, the invention relates to systems and methods for increasing overall carbon capture in processes of producing products by microbial fermentation of substrates, said systems and methods including at least one CO2 removal process performed on substrates and/or streams before (i.e., upstream) or after (i.e., downstream) the fermentation reaction. In certain embodiments of the invention, the substrate comprises CO. Typically, the substrate will be gaseous; however, the invention is not limited thereto.

In one aspect, the invention relates to systems and methods for increasing the efficiency of processes of producing products by microbial fermentation of gases, said systems and methods including at least one gas separation process performed on the gases before (i.e., upstream) or after (i.e., downstream) the fermentation reaction. As noted above, in particular embodiments, the substrate gas used in microbial fermentation comprises CO; however, the invention is not limited thereto.

In another particular aspect the invention relates to systems and methods for increasing the efficiency of processes of producing products by microbial fermentation of gases, particularly where the supply of the gases is intermittent in nature. In particular embodiments, the substrate gas used in microbial fermentation comprises CO; however, the invention is not limited thereto.

The invention further provides methods and systems for the production of alcohol using microbial fermentation. These methods and systems involve the use of waste gases from an industrial process, such as the manufacture of steel, in the fermentation reaction, wherein no or only minimal additional processing steps are performed on the gases prior to such use. In certain embodiments, waste gases from one or more industrial processes and/or alternative sources are combined or blended to provide a stream with a desirable or optimised composition to the fermentation reaction.

The invention also provides methods and systems for optimising the composition of a substrate stream comprising CO derived, at least in part, from an industrial process such as the manufacture of steel.

The invention also provides methods for the production of alcohol using microbial fermentation and methods for increasing the efficiency of alcohol production using microbial fermentation. In one embodiment, these methods involve utilising scrubber water from an industrial process in the fermentation reaction.

While certain embodiments of the invention, namely those that include the production of ethanol by anaerobic fermentation using CO as the primary substrate, are readily recognized as being valuable improvements to technology of great interest today, it should be appreciated that the invention is applicable to production of alternative products such as other alcohols and the use of alternative substrates, particularly gaseous substrates, as will be known by persons of ordinary skill in the art to which the invention relates upon consideration of the instant disclosure. For example, gaseous substrates containing carbon dioxide and hydrogen may be used in particular embodiments of the invention. Further, the invention may be applicable to fermentations to produce acetate, butyrate, propionate, caproate, ethanol, propanol, and butanol, and hydrogen. By way of example, these products may be produced by fermentation using microbes from the genus *Moorella, Clostridia, Ruminococcus, Acetobacterium, Eubacterium, Butyribacterium, Oxobacter, Methanosarcina, Methanosarcina*, and *Desulfotomaculum*.

Certain embodiments of the invention are adapted to use gas streams produced by one or more industrial processes. Such processes include steel making processes, particularly processes which produce a gas stream having a high CO content or a CO content above a predetermined level (i.e., 5%). According to such embodiments, carboxydotrophic bacteria are preferably used to produce acids and/or alcohols, particularly ethanol or butanol, within one or more bioreactors. Those skilled in the art will be aware upon consideration of the instant disclosure that the invention may be applied to various industries or waste gas streams, including those of vehicles with an internal combustion engine. Also, those skilled in the art will be aware upon consideration of the instant disclosure that the invention may be applied to other fermentation reactions including those using the same or different micro-organisms. It is therefore intended that the scope of the invention is not limited to the particular embodiments and/or applications described but is instead to be understood in a broader sense; for example, the source of the gas stream is not limiting, other than that at least a component thereof is usable to feed a fermentation reaction. The invention has particular applicability to improving the overall carbon capture and/or production of ethanol and other alcohols from gaseous substrates such as automobile exhaust gases and high volume CO-containing industrial flue gases.

Fermentation

Processes for the production of ethanol and other alcohols from gaseous substrates (such as those described in the background section above) are known. Exemplary processes include those described for example in WO 2007/117157 and WO 2008/115080, as well as U.S. Pat. Nos. 6,340,581, 6,136,577, 5,593,886, 5,807,722 and 5,821,111, each of which is incorporated herein by reference.

A number of anaerobic bacteria are known to be capable of carrying out the fermentation of CO to alcohols, including n-butanol and ethanol, and acetic acid, and are suitable for use in the process of the present invention. Examples of such bacteria that are suitable for use in the invention include those of the genus *Clostridium*, such as strains of *Clostridium ljungdahlii*, including those described in WO 00/68407, EP 117309, U.S. Pat. Nos. 5,173,429, 5,593,886, and 6,368,819, WO 98/00558 and WO 02/08438, *Clostridium carboxydivorans* (Liou et al., International Journal of Systematic and Evolutionary Microbiology 33: pp 2085-2091) and *Clostridium autoethanogenum* (Abrini et al., Archives of Microbiology 161: pp 345-351). Other suitable bacteria include those of the genus *Moorella*, including *Moorella* sp HUC22-1 (Sakai et al., Biotechnology Letters 29: pp 1607-1612), and those of the genus *Carboxydothermus* (Svetlichny, V. A., et al. (1991), Systematic and Applied Microbiology 14: 254-260). The disclosures of each of these publications are incorporated herein by reference. In addition, other carboxydotrophic anaerobic bacteria can be used in the processes of the invention by a person of skill in the art. It will also be appreciated upon consideration of the instant disclosure that a mixed culture of two or more bacteria may be used in processes of the present invention.

Culturing of the bacteria used in a method of the invention may be conducted using any number of processes known in the art for culturing and fermenting substrates using anaerobic bacteria. Exemplary techniques are provided in the "Examples" section below. By way of further example, those processes generally described in the following articles using gaseous substrates for fermentation may be utilised: (i) K. T. Klasson, et al. (1991). Bioreactors for synthesis gas fermentations resources. Conservation and Recycling, 5; 145-165; (ii) K. T. Klasson, et al. (1991). Bioreactor design for synthesis gas fermentations. Fuel. 70. 605-614; (iii) K. T. Klasson, et al. (1992). Bioconversion of synthesis gas into liquid or gaseous fuels. Enzyme and Microbial Technology. 14; 602-608; (iv) J. L. Vega, et al. (1989). Study of Gaseous Substrate Fermentation Carbon Monoxide Conversion to Acetate. 2. Continuous Culture. Biotech. Bioeng. 34. 6. 785-793; (vi) J. L. Vega, et al. (1989). Study of gaseous substrate fermentations: Carbon monoxide conversion to acetate. 1. Batch culture. Biotechnology and Bioengineering. 34. 6. 774-784; (vii) J. L. Vega, et al. (1990). Design of Bioreactors for Coal Synthesis Gas Fermentations. Resources, Conservation and Recycling. 3. 149-160; all of which are incorporated herein by reference.

One exemplary micro-organism suitable for use in the present invention is *Clostridium autoethanogenum*. In one embodiment, the *Clostridium autoethanogenum* is a *Clostridium autoethanogenum* having the identifying characteristics of the strain deposited at the German Resource Centre for Biological Material (DSMZ) under the identifying deposit number 19630. In another embodiment, the *Clostridium autoethanogenum* is a *Clostridium autoethanogenum* having the identifying characteristics of DSMZ deposit number DSMZ 10061.

The fermentation may be carried out in any suitable bioreactor. In some embodiments of the invention, the bioreactor may comprise a first, growth reactor in which the micro-organisms are cultured, and a second, fermentation reactor, to which fermentation broth from the growth reactor is fed and in which most of the fermentation product (e.g. ethanol and acetate) is produced.

According to various embodiments of the invention, the carbon source for the fermentation reaction is a gaseous substrate containing CO. The gaseous substrate may be a CO-containing waste gas obtained as a by-product of an industrial process, or from some other source such as from automobile exhaust fumes. In certain embodiments, the industrial process is selected from the group consisting of ferrous metal products manufacturing, such as is conducted in a steel mill, non-ferrous products manufacturing, petroleum refining processes, gasification of coal, electric power production, carbon black production, ammonia production, methanol production and coke manufacturing. In these embodiments, the CO-containing gas may be captured from the industrial process before it is emitted into the atmosphere, using any convenient method. Depending on the composition of the gaseous CO-containing substrate, it may also be desirable to treat it to remove any undesired impurities, such as dust particles before introducing it to the fermentation. For example, the gaseous substrate may be filtered or scrubbed using known methods.

The CO-containing gaseous substrate will ideally contain a significant proportion of CO, such as at least 5% to about 100% CO by volume, or from 20% to 95% CO by volume, or from 40% to 95% CO by volume, or from 60% to 90% CO by volume or from 70% to 90% CO by volume. Gaseous substrates having lower concentrations of CO, such as 6%, may also be appropriate, particularly when H2 and CO2 are also present.

While it is not necessary for the gaseous substrate to contain any hydrogen, the presence of hydrogen will generally not be detrimental to product formation in accordance with methods of the invention. However, in certain embodiments of the invention, the gaseous substrate is substantially hydrogen free (less than 1%). The gaseous substrate may also contain some CO2, such as about 1% to about 30% by volume, or such as about 5% to about 10% CO2.

As noted previously, the presence of hydrogen in the substrate stream can lead to an improvement in efficiency of overall carbon capture and/or ethanol productivity. For example, WO0208438 describes the production of ethanol using gas streams of various compositions. In one preferred embodiment, a substrate stream comprising 63% H2, 32% CO and 5% CH4 was provided to a culture of *C. ljungdahlii* in a bioreactor to promote microbial growth and ethanol production. When the culture reached a steady state and microbial growth was no longer the main objective, the substrate stream was switched to 15.8% H2, 36.5% CO, 38.4% N2 and 9.3% CO2 in order to provide CO in a slight excess and promote ethanol production. This document also describes gas streams with higher and lower CO and H2 concentrations.

Accordingly, it may be necessary to alter the composition of the substrate stream in order to improve alcohol production and/or overall carbon capture. Additionally or alternatively, the composition may be altered (i.e. CO, CO2 and/or H2 levels adjusted) to optimise the efficiency of the fermentation reaction and ultimately improve alcohol production and/or overall carbon capture.

In some embodiments, the CO-containing gaseous substrate may be sourced from the gasification of organic matter such as methane, ethane, propane, coal, natural gas, crude oil, low value residues from oil refinery (including petroleum coke or petcoke), solid municipal waste or biomass. Biomass includes by-products obtained during the extraction and processing of foodstuffs, such as sugar from sugarcane, or starch from maize or grains, or non-food biomass waste generated by the forestry industry. Any of these carbonaceous materials can be gasified, i.e. partially combusted with oxygen, to produce synthesis gas (syngas comprising significant amounts of H2 and CO). Gasification processes typically produce a synthesis gas with a molar ratio of H2 to CO of about 0.4:1 to 1.2:1, together with lesser amounts of CO2, H2S, methane and other inert substances. The ratio of the gas produced can be varied by means known in the art and are described in detail in WO200701616. However, by way of example, the following gasifier conditions can be altered to adjust the CO:H2 product ratio: feedstock composition (particularly C:H ratio), operating pressure, temperature profile (influencing quench of product mix) and oxidant employed (air, oxygen enriched air, pure O2 or steam; wherein steam tends to result in higher CO:H2 ratios). Accordingly, the operating conditions of the gasifier can be adjusted to provide a substrate stream with a desirable composition for fermentation or blending with one or more other streams to provide an optimised or desirable composition for increased alcohol productivity and/or overall carbon capture in a fermentation process.

In other embodiments, the substrate comprising CO can be derived from the steam reforming of hydrocarbons. Hydrocarbons, such as natural gas hydrocarbons can be reformed at high temperature to yield CO and H2 according to the following:

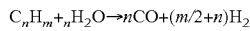
$$C_nH_m + nH_2O \rightarrow nCO + (m/2+n)H_2$$

By way of example, steam methane reforming involves reacting steam with methane to produce CO and H2 at elevated temperature (700-1100° C.) in the presence of a nickel catalyst. The resulting stream (comprising 1 mol CO and 3 mol H2 for every mol CH4 converted) can be passed directly to the fermenter or blended with a substrate stream from another source to increase ethanol productivity and/or overall carbon capture in a fermentation process. Alcohols such as methanol can also be reformed to produce CO2 and H2 that may be used in a similar manner.

In another embodiment, the substrate comprising CO is derived from the steel manufacturing process. In the steel making process, iron ore is crushed and pulverised, subjected to pre-treatments such as sintering or pelletizing, and then passed to a blast furnace (BF), where it is smelted. In the smelting process, coke serves as the source of carbon, which works as a reducing agent to reduce the iron ore. Coke acts as the heat source for heating and melting the materials. The hot metal is decarburised in a basic oxygen furnace (BOF) by injecting a high-velocity jet of pure oxygen against the surface of the hot metal. The oxygen reacts directly with carbon in the hot metal to produce carbon monoxide (CO). Thus, a gas stream with a high CO content is exhausted from the BOF. According to certain embodiments of the invention, this stream is used to feed one or more fermentation reactions. However, as would be apparent to one of skill in the art, CO may be produced elsewhere within the steel making process, and according to various embodiments of the invention, such alternative sources may be used instead of or in combination with exhaust gases from the BOF. Depending on the source (i.e., the particular stage within the steel making process), the CO content of the gases exhausted thereby may vary. Also, there may be periods when there are breaks in one or more of such streams, particularly in batch processing plants.

Typically, streams exhausted from the steel mill decarburisation process comprise a high concentration of CO and low concentrations of H2. While such streams can be directly passed to the bioreactor with little or no further treatment, it may be desirable to optimise the composition of the substrate stream in order to achieve higher efficiency of alcohol production and/or overall carbon capture. For example, the concentration of H2 in the substrate stream may be increased before the stream is passed to the bioreactor.

According to particular embodiments of the invention, streams from two or more sources can be combined and/or blended to produce a desirable and/or optimised substrate stream. For example, a stream comprising a high concentration of CO, such as the exhaust from a steel mill converter, can be combined with a stream comprising high concentrations of H2, such as the off-gas from a steel mill coke oven.

An early stage of the steel making process typically involves the reduction of iron ore using coke. Coke is a solid carbon fuel source used to melt and reduce iron ore and is typically produced on-site at a steel mill. In the coke-making process, bituminous coal is fed into a series of ovens, which are sealed and heated at high temperatures in the absence of oxygen, typically in cycles lasting 14 to 36 hours. The solid carbon remaining in the oven is coke. It is taken to the quench tower, where it is cooled with a watery spray or by circulating an inert gas (nitrogen), then screened and sent to the blast furnace.

The volatile compounds produced during this process are generally processed to remove tar, ammonia, naphthalene, phenol, light oils and sulphur before the gas is used as fuel to heat ovens. Gas produced as a result of coke production typically has a high H2 content (typical composition: 55% H2, 25% CH4, 6% CO, 3% N2, 2% other hydrocarbons). As such, at least a portion of the coke oven gas may be diverted to the fermentation process for blending with a stream comprising CO, to improve alcohol productivity and/or overall carbon capture. It may be necessary to treat the coke oven gas prior to passing it to the fermenter to remove by-products that may be toxic to the culture.

Alternatively or additionally, an intermittent stream comprising CO, such as an exhaust stream from the converter, may be combined with and/or blended with a substantially continuous stream comprising CO and optionally H2, such as syngas produced in a gasification process as described previously. In certain embodiments, this would maintain the provision of a substantially continuous substrate stream to the bioreactor. In a particular embodiment, the stream produced by the gasifier may be increased and/or decreased in accordance with the intermittent production of CO from an industrial source in order to maintain a substantially continuous substrate stream with a desirable or optimised composition. In another embodiment, the gasifier conditions may be altered as described previously in order to increase or decrease the CO:H2 ratio, in accordance with the intermittent production of CO from an industrial source, in order to maintain a substantially continuous substrate stream with a desirable or optimised CO and H2 composition.

Typically, the substrate streams used in the invention will be gaseous; however, the invention is not limited thereto. For example, the carbon monoxide may be provided to a bioreactor in a liquid. For example, a liquid may be saturated with a carbon monoxide containing gas and then that liquid added to a bioreactor. This may be achieved using standard methodology. By way of example, a microbubble dispersion generator (Hensirisak et al., Scale-up of microbubble dispersion generator, for aerobic fermentation; Applied Biochemistry and Biotechnology Volume 101, Number 3, October, 2002) could be used for this purpose.

It will be appreciated that for growth of the bacteria and CO-to-ethanol fermentation to occur, in addition to the CO-containing substrate gas, a suitable liquid nutrient medium will need to be fed to the bioreactor. A nutrient medium will contain vitamins and minerals sufficient to permit growth of the micro-organism used. Anaerobic media suitable for the fermentation of ethanol using CO as the sole carbon source are known in the art. For example, suitable media are described in U.S. Pat. Nos. 5,173,429 and 5,593,886 and WO 02/08438, WO2007/115157 and WO2008/115080, referred to above. The "Examples" herein provide other exemplary media.

The fermentation should desirably be carried out under appropriate conditions for the desired fermentation to occur (e.g. CO-to-alcohol). Reaction conditions that should be considered include pressure, temperature, gas flow rate, liquid flow rate, media pH, media redox potential, agitation rate (if using a continuous stirred tank reactor), inoculum level, maximum gas substrate concentrations to ensure that CO in the liquid phase does not become limiting, and maximum product concentrations to avoid product inhibition.

The optimum reaction conditions will depend partly on the particular micro-organism used. However, in general, it may be preferable that the fermentation be performed at a pressure higher than ambient pressure. Operating at increased pressures allows a significant increase in the rate of CO transfer from the gas phase to the liquid phase where it can be taken up by the micro-organism as a carbon source for the production of ethanol. This in turn means that the retention time (defined as the liquid volume in the bioreactor divided by the input gas flow rate) can be reduced when bioreactors are maintained at elevated pressure rather than atmospheric pressure.

Also, because a given CO-to-ethanol conversion rate is in part a function of the substrate retention time, and achieving a desired retention time in turn dictates the required volume of a bioreactor, the use of pressurized systems can greatly reduce the volume of the bioreactor required, and consequently the capital cost of the fermentation equipment. According to examples given in U.S. Pat. No. 5,593,886, reactor volume can be reduced in linear proportion to increases in reactor operating pressure, i.e. bioreactors operated at 10 atmospheres of pressure need only be one tenth the volume of those operated at 1 atmosphere of pressure.

The benefits of conducting a gas-to-ethanol fermentation at elevated pressures have also been described elsewhere. For example, WO 02/08438 describes gas-to-ethanol fermentations performed under pressures of 30 psig and 75 psig, giving ethanol productivities of 150 g/l/day and 369 g/l/day respectively. However, example fermentations performed using similar media and input gas compositions at atmospheric pressure were found to produce between 10 and 20 times less ethanol per liter per day.

It is also desirable that the rate of introduction of the CO-containing gaseous substrate is such as to ensure that the concentration of CO in the liquid phase does not become limiting. This is because a consequence of CO-limited conditions may be that the ethanol product is consumed by the culture.

Product Recovery

The products of the fermentation reaction can be recovered using known methods. Exemplary methods include those described in WO2007/117157, WO2008/115080 and U.S. Pat. Nos. 6,340,581, 6,136,577, 5,593,886, 5,807,722 and 5,821,111. However, briefly and by way of example only, ethanol may be recovered from the fermentation broth by methods such as fractional distillation or evaporation, and extractive fermentation.

Distillation of ethanol from a fermentation broth yields an azeotropic mixture of ethanol and water (i.e. 95% ethanol and 5% water). Anhydrous ethanol can subsequently be obtained through the use of molecular sieve ethanol dehydration technology, which is also well known in the art.

Extractive fermentation procedures involve the use of a water-miscible solvent that presents a low toxicity risk to the fermentation organism, to recover the ethanol from the dilute fermentation broth. For example, oleyl alcohol is a solvent that may be used in this type of extraction process. In this process, oleyl alcohol is continuously introduced into a fermenter, whereupon this solvent rises forming a layer at the top of the fermenter which is continuously extracted and fed through a centrifuge. Water and cells are then readily separated from the oleyl alcohol and returned to the fermenter while the ethanol-laden solvent is fed into a flash vaporization unit. Most of the ethanol is vaporized and condensed while the non volatile oleyl alcohol is recovered for re-use in the fermentation.

Acetate may also be recovered from the fermentation broth using methods known in the art. For example, an adsorption system involving an activated charcoal filter may be used. In this case, microbial cells are typically first removed from the fermentation broth using a suitable separation method. Numerous filtration-based methods of generating a cell free fermentation broth for product recovery are known in the art. The cell free ethanol—and acetate—containing permeate is then passed through a column containing activated charcoal to adsorb the acetate. Acetate in the acid form (acetic acid) rather than the salt (acetate) form is more readily adsorbed by activated charcoal. It is therefore preferred that the pH of the fermentation broth be reduced to less than about 3 before it is passed through the activated charcoal column, to convert the majority of the acetate to the acetic acid form.

Acetic acid adsorbed to the activated charcoal may be recovered by elution using methods known in the art. For example, ethanol may be used to elute the bound acetate. In certain embodiments, ethanol produced by the fermentation process itself may be used to elute the acetate. Because the boiling point of ethanol is 78.8° C. and that of acetic acid is 107° C., ethanol and acetate can readily be separated from each other using a volatility-based method such as distillation.

Other methods for recovering acetate from a fermentation broth are known in the art and may be used in processes of the present invention. For example, U.S. Pat. Nos. 6,368,819 and 6,753,170 describe a solvent and cosolvent system that can be used for extraction of acetic acid from fermentation broths. As with the oleyl alcohol-based system described above for the extractive fermentation of ethanol, the systems described in U.S. Pat. Nos. 6,368,819 and 6,753,170 describe a water immiscible solvent/co-solvent that can be mixed with the fermentation broth in either the presence or absence of the fermented micro-organisms to extract the acetic acid. The solvent/co-solvent containing the acetic acid is then separated from the broth by distillation. A second distillation step may then be used to purify the acetic acid from the solvent/co-solvent system.

The products of the fermentation reaction (for example ethanol and acetate) may be recovered from the fermentation broth by continuously removing a portion of the broth from the fermentation bioreactor, separating microbial cells from the broth (conveniently by filtration), and recovering one or more products from the broth simultaneously or sequentially. Ethanol may conveniently be recovered by distillation, and acetate may be recovered by adsorption on activated charcoal, using the methods described above. The separated microbial cells can be returned to the fermentation bioreactor. The cell free permeate remaining after the ethanol and acetate have been removed can also be returned to the fermentation bioreactor. Additional nutrients (such as B vitamins) may be added to the cell free permeate to replenish the nutrient medium before it is returned to the bioreactor. Also, if the pH of the broth was adjusted as described above to enhance adsorption of acetic acid to the activated charcoal, the pH should be re-adjusted to a similar pH to that of the broth in the fermentation bioreactor, before being returned to the bioreactor.

$CO_2$ Removal

According to certain embodiments of the invention, the system used for CO2 removal includes a means for selectively separating CO2 from a mixed stream and a means for converting the CO2 to products and/or preparing the CO2 for storage or further use. Alternatively, the process includes a means for converting the CO2 in a stream directly to products and/or substances suitable for storage or further use.

In one embodiment, CO2 is selectively separated from a mixed gas stream using any separation means known in the art such as the exemplary methods provided below. Other methods of CO2 separation that may be used in embodiments of the invention include extraction with a metal oxide, such as CaO, and use of porous carbon or selective solvent extraction such as amine extraction.

Amines such as aqueous monoethanolamine (MEA), diglycolamine (DGA), diethanolamine (DEA), diisopropanolamine (DIPA) and methyldiethanolamine (MDEA) are widely used industrially for removing $CO_2$ and hydrogen sulfide from natural gas streams and refinery process streams.

The $CO_2$ separated in such processes may be permanently stored. Many examples of permanent $CO_2$ storage are known in the art, such as geological storage (geo-sequestration), ocean storage and mineral storage (e.g. conversion to metal carbonates).

Geological storage involves injecting carbon dioxide, generally in supercritical form, directly into underground geological formations. Oil fields, gas fields, saline formations, unminable coal seams, and saline-filled basalt formations have been suggested as storage sites. Various physical (e.g., highly impermeable caprock) and geochemical trapping mechanisms can be used to prevent the $CO_2$ from escaping to the surface. For well-selected, designed and managed geological storage sites, the Intergovernmental Panel on Climate Change estimates that $CO_2$ could be trapped for millions of years, and the sites are likely to retain over 99% of the injected $CO_2$ over 1,000 years.

Several options for ocean storage have been proposed: (i) 'dissolution' injection of $CO_2$ by ship or pipeline into the water at depths of 1000 m or more, and the $CO_2$ subsequently dissolves; (ii) 'lake' deposition of $CO_2$ directly onto the sea floor at depths greater than 3000 m, where $CO_2$ is denser than water and is expected to form a 'lake' that would delay dissolution of $CO_2$ into the environment; (iii) conversion of the $CO_2$ to bicarbonates (using limestone); and (iv) storage of the $CO_2$ in solid clathrate hydrates already existing on the ocean floor, or use in growing more solid clathrate.

In mineral storage, $CO_2$ is exothermically reacted with abundantly available metal oxides to produce stable carbonates. This process occurs naturally over many years and is responsible for much of the surface limestone. The reaction rate can be made faster, for example by reacting at higher temperatures and/or pressures, or by pre-treatment of the minerals, although this method can require additional energy.

Alternatively, the separated $CO_2$ may be used to make products, such as direct or indirect conversion to hydrocarbons. A well-known process to produce a hydrocarbon is the process for making methanol from $CO_2$ and $H_2$. Catalytic or electrochemical dissociation of water to produce oxygen and hydrogen ions, wherein the hydrogen ions can be used to convert $CO_2$ to hydrocarbons is also known in the art. If $CO_2$ is heated to 2400° C., it splits into carbon monoxide and oxygen. The Fischer-Tropsch process can then be used to convert the CO into hydrocarbons. In such processes, the CO may be returned to the fermentation process. By way of example, the required temperature can be achieved by using a chamber containing a mirror to focus sunlight on the gas. Alternatively, the separated $CO_2$ may be used in further fermentation(s) to produce products. Those skilled in the art will appreciate there are many examples of microbial fermentation reactions that convert $CO_2$ into products. For example, $CO_2$ may be converted into methane by anaerobic fermentation using methanogenic microbes. Examples of this and other related fermentation processes are disclosed in the aforementioned WO2006/108532. Further examples of fermentation reactions using $CO_2$ to produce products are provided in the aforementioned WO2007/117157 and WO2008/115080.

$CO_2$ is also a desirable feedstock in syngas production. $CO_2$ can be supplied to the reformer (gasifier) to reduce methane consumption and improve/increase the $H_2$:CO ratio. Accordingly, in one embodiment, at least a portion of the separated $CO_2$ may be supplied to a gasifier integrated into the fermentation process.

In another embodiment of the invention, the separated $CO_2$ may be converted to products such as concrete cement. In a process mimicking marine cement produced by coral when making their shells and reefs, magnesium and/or calcium can be combined with $CO_2$ to produce carbonates.

$CO_2$ is also readily absorbed by algae in a photosynthetic process, which can be used to capture carbon from waste streams. Algae rapidly grow in the presence of $CO_2$ and sunlight and can be harvested and converted into products such as biodiesel and/or alcohol.

Alternatively, the $CO_2$ may be directly captured from a stream without the need of an additional separation step. For example, in a particular embodiment, a stream, preferably a gaseous stream, comprising $CO_2$ may be passed through a second fermentation process to convert $CO_2$ to products.

Gas Separation

According to certain embodiments of the invention, the process used for gas separation comprises one or more steps of cryogenic fractionation, molecular sieving, adsorption, pressure swing adsorption, or absorption. Whatever process is used, gas separation can be performed to isolate at least a portion of one or more of the following components: $H_2$, $O_2$, $CO_2$ and CO, from the gas stream. Additionally or alternatively, gas separation according to embodiments of the invention may be used to remove one or more portions from the gas stream (e.g. $N_2$, $O_2$) so that the remainder may be more efficiently used, such as in the bioreactor.

Adsorption is the accumulation of gases, liquids or solutes on the surface of a solid or liquid. Absorption is the process by which one substance, such as a solid or liquid, takes up another substance, such as a liquid or gas, through minute pores or spaces between its molecules.

Pressure swing adsorption (PSA) is an adiabatic process which may be used for the purification of gases to remove accompanying impurities by adsorption through suitable adsorbents in fixed beds contained in pressure vessels under high pressure. Regeneration of adsorbents is accomplished by countercurrent depressurization and by purging at low pressure with previously recovered near product quality gas. To obtain a continuous flow of product, preferably at least two adsorbers are provided, such that at least one adsorber is receiving a gas stream (such as a waste/exhaust/biogas gas stream) and actually produces a product of desired purity. Simultaneously, the subsequent steps of depressurization, purging and repressurization back to the adsorption pressure are executed by the other adsorber(s). Common adsorbents may readily be selected by one of skill in the art dependent on the type of impurity to be adsorbed and removed. Suitable adsorbents include zeolitic molecular sieves, activated carbon, silica gel or activated alumina. Combinations of adsorbent beds may be used on top of one another, thereby dividing the adsorber contents into a number of distinct zones. Pressure swing adsorption involves a pendulating swing in parameters such as pressure, temperature, flow and composition of gaseous and adsorbed phase.

Purification or separation of gases using PSA normally takes place at near ambient feed gas temperatures, whereby the components to be removed are selectively adsorbed. Adsorption should ideally be sufficiently reversible to enable regeneration of adsorbents at similar ambient temperature. PSA may be used for treatment and/or purification of most common gases including CO, $CO_2$ and $H_2$. Examples of Pressure Swing Adsorption techniques are described in detail in Ruthven, Douglas M. et al., 1993 *Pressure Swing Adsorption*, John Wiley and Sons.

A molecular sieve is a material containing tiny pores of a precise and uniform size that is used as an adsorbent for gases and liquids. Molecules that are small enough to pass through the pores are adsorbed while larger molecules are not. A molecular sieve is similar to a common filter but operates on a molecular level. Molecular sieves often consist of aluminosilicate minerals, clays, porous glasses, microporous charcoals, zeolites, active carbons, or synthetic compounds that have open structures through which small molecules, such as nitrogen and water, can diffuse. Methods for regeneration of molecular sieves include pressure changing (e.g. in oxygen concentrators) and heating and purging with a carrier gas.

Membranes may be used, for example, to separate hydrogen from gases like nitrogen and methane, to recover hydrogen, to separate methane from biogas, or to remove water vapour, CO2, H2S or volatile organic liquids. Different membranes, including porous and non-porous membranes, may be selected to serve the desired purpose as would be apparent to one of skill in the art upon consideration of the instant disclosure. For example, a Palladium membrane permits transport solely of H2. In a particular embodiment, CO2 can be separated from a stream, using a CO2 permeable membrane. The CO2 separated from the stream can be passed to a CO2 remover such as the gasifier discussed previously.

Cryogenic fractionation involves compressing the gas stream and cooling it to a temperature low enough to allow separation by distillation. It may be used, for example, to remove CO2. Certain components (e.g. water) are typically removed from the stream prior to performing cryogenic fractionation.

The same techniques can also be used to remove oxygen from a gaseous stream to produce CO and/or CO2-rich anaerobic streams. In addition, oxygen can be removed biologically, by, for instance, passing the combustion exhaust gas into a sealed fermenter containing facultative aerobic micro-organisms, a reduced carbon substrate, and the necessary nutrients for the micro-organisms. The facultative aerobic micro-organisms can consume oxygen to create CO and/or CO2-rich anaerobic streams.

Alternative methods for separating or removing O2 from a gaseous stream are also well known in the art. However, by way of example, oxygen can be simply reduced and/or removed using hot copper or a catalytic converter.

Tailoring the gas separation process to a particular source of gas can make an otherwise non-commercially viable bioconversion process commercially viable. For example, with appropriate separation of CO from a car exhaust stream, a usable energy source may be obtained from the stream and unwanted gas emissions can be reduced. According to one embodiment of the invention, the gaseous substrate comprises Syngas containing CO and H2, and gas separation is performed to remove hydrogen from the stream so that it may be isolated and used as a fuel outside of the fermentation process. The CO may be used to feed the fermentation reaction.

Intermittent Gas Streams

According to various aspects of the invention, the fermentation substrate is derived from an industrial source. Typically, substrates derived from industrial sources are gaseous and such gases may vary in composition and/or pressure and in some instances may be intermittent in nature. In certain embodiments, the invention provides means to improve or "smooth" supply of a gaseous substrate to a bioreactor for fermentation to produce products, particularly in instances where the substrate supply is intermittent or non-continuous in nature. Any known means for improving continuity or "smoothing" of a gaseous substrate stream may be used; however, particular embodiments of the invention include processes or systems that include at least one buffering means adapted to receive an intermittent substrate stream, and to deliver a substantially continuous substrate stream to a bioreactor.

In particular embodiments, the buffering means includes a storage tank adapted to receive intermittent gas streams. The intermittent stream may be compressed prior to entering the storage tank; alternatively, the storage tank may be configured to expand as it receives the substrate stream. For example, the buffer storage tank may include a 'floating roof' adapted to rise and fall to accommodate a gaseous substrate. Floating roof type storage tanks are known in the art, such as those used to accommodate supply and demand fluctuations in gas supply. The storage tank may be adapted to supply a substantially continuous substrate stream to a fermentation bioreactor, and as such may include a means for controlling the rate of flow of the stream exiting the tank.

In such embodiments, the storage tank serves as a substrate reservoir. However, according to an alternative embodiment, the buffer storage tank may be substituted by an alternative form of storage that performs the same function. For example, alternative forms may include one or more of absorption, adsorption, and pressure and/or temperature swings. Additionally or alternatively, the substrate may be dissolved in a liquid in the reservoir or held in a matrix, such as a porous solid material, until it is required. In particular embodiments of the invention, the substrate may be dissolved in a liquid in the storage tank and delivered directly to the bioreactor in solution when required.

Alternatively, the bioreactor itself may be configured such that the headspace above a fermentation liquid nutrient medium acts as a buffer for the intermittent stream. For example, the system may include a means to compress the gaseous substrate stream (when available) and pass it to the bioreactor. The pressure in the headspace in the bioreactor will increase when additional substrate is provided. The substrate is thus continuously available for conversion to products by microbial fermentation.

In another embodiment, the system may be adapted to receive gaseous substrate streams from multiple intermittent sources. Such a system may include means to combine and/or switch between streams to provide a substantially continuous substrate stream to the bioreactor.

Micro-organisms used in the fermentation reaction typically have an allowable temperature range, above or below which the reaction rate slows significantly. As such, the system may include cooling means, wherein when availability of the substrate stream is limited, the media in the bioreactor can be cooled to slow down the fermentation reaction and reduce demand for the substrate. Conversely, when the availability of the substrate stream increases, the temperature inside the bioreactor can be increased toward the upper end of the temperature range to increase the reaction rate.

Alternatively or additionally, a cooling means may be configured to even the cooling load so as to reduce the peak cooling load on a fermentation system. For example, assume that the cooling load required to cope with heat within a gas feed stream and/or a fermentation exotherm in a predetermined period (while gas is being processed) is 2 MW. To maintain the contents of the fermentation tank at a constant temperature during this period, heat must be removed at this rate to maintain a constant temperature within the tank. Conversely, during periods when there is no gas being processed and the exotherm essentially ceases, the cooling load will be zero. Thus, particularly for large-scale industrial applications, there will be periods when the cooling load is very high, which imposes significant constraints on the system. By levelling the cooling load, the maximum required cooling rate is reduced. Thus, it is possible to operate with a smaller scale cooling system, although on a continuous (or more continuous) basis.

Using the parameters of the previous example but assuming that the periods when gas is, and those when gas is not, processed are of equal duration, then heat may be removed from the fermentation tank continuously at 1 MW. Under these conditions, the heat removal rate when gas is being processed will not keep up with the heat input/generation, and the temperature within the fermentation tank will rise. When the gas is stopped, but cooling continues, the temperature within the fermentation tank will drop. In this way, a cooling system sized for 1 MW continuous load is required rather than a system sized for a 2 MW load that only runs half of the time. However, the temperature rise and subsequent drop must be limited to maintain the temperature inside the tank within the allowable range for the micro-organisms. Thus, according to particular embodiments, while not constant, the cooling load may be "smoothed," so that variations therein may be more gradual and/or more limited, in that there is a smaller difference between the maximum and minimum cooling loads.

Industrial Off Gas as a Resource for Fermentation

In accordance with other aspects of the invention, industrial waste gases are used in a fermentation reaction with no or only minimal additional scrubbing or pre-treatment steps being used to make the gases suitable therefor.

The waste gases may result from any number of industrial processes. The invention has particular applicability to supporting the production of ethanol from gaseous substrates such as high volume CO-containing industrial flue gases. Examples include gases produced during ferrous metal products manufacturing, non-ferrous products manufacturing, petroleum refining processes, gasification of coal, gasification of biomass, electric power production, carbon black production, ammonia production, methanol production and coke manufacturing. In a particular embodiment of the invention, the waste gases are generated during a process for making steel. For example, those skilled in the art will appreciate the waste gases produced during various stages of the steel making process have high CO and/or CO2 concentrations. In particular, the waste gas produced during the decarburisation of steel in various methods of steel manufacturing, such as in an oxygen converter (e.g. BOF or KOBM), has a high CO content and low O2 content making it a suitable substrate for anaerobic carboxydotrophic fermentation.

Waste gases produced during the carburisation of steel are optionally passed through water to remove particulate matter before passing to a waste stack or flue for directing the waste gas into the atmosphere. Typically, the gases are driven into the waste stack with one or more fans.

In particular embodiments of the invention, at least a portion of the waste gas produced during the decarburisation of steel is diverted to a fermentation system by suitable conduit means. By way of example, piping or other transfer means can be connected to the waste gas stack from a steel mill to divert at least a portion of the waste gas to a fermentation system. Again, one or more fans can be used to divert at least a portion of the waste gas into the fermentation system. In particular embodiments of the invention, the conduit means is adapted to provide at least a portion of the waste gas produced during the decarburisation of steel to a fermentation system.

The control of and means for feeding gases to a bioreactor will be readily apparent to those of ordinary skill in the art to which the invention relates.

While steel mills can be adapted to substantially continuously produce steel and subsequently waste gases, particular aspects of the process may be intermittent. Typically the decarburisation of steel is a batch process lasting several minutes to several hours. As such, the conduit means may be adapted to divert at least a portion of the waste gas, such as the gas produced during the decarburisation of steel, to the fermentation system if it is determined the waste gas has a desirable composition.

The pH of the contents of the bioreactor used in the fermentation process may be adjusted as required. The appropriate pH will be dependent on the conditions required for a particular fermentation reaction having regard to the nutrient media and micro-organisms used, as will be appreciated by persons of ordinary skill in the art to which the invention relates. In one preferred embodiment, in fermentation of a gaseous substrate containing CO utilising *Clostridium autoethanogenum*, the pH may be adjusted to approximately 5.5 to 6.5, most preferably to approximately 5.5. Further examples include pH 5.5 to 6.5 using *Moorella thermoacetica* for the production of acetic acid, pH 4.5 to 6.5 using *Clostridium acetobutylicum* for the production of butanol, and pH 7 using *Carboxydothermus hygrogenaformans* for the production of hydrogen. Those skilled in the art will be aware of suitable means for maintaining the bioreactor at the required pH. However, by way of example, aqueous bases such as NaOH and aqueous acids such as H2SO4 can be used to raise and lower the pH of the fermentation medium and maintain the desired pH.

An additional benefit of the invention is that, because there is no or only minimal scrubbing and/or other treatment processes performed on the waste gases prior to their use in a fermentation reaction, the gases will contain additional material resulting from the industrial process, which additional material may be used, at least in part, as a feedstock for the fermentation reaction.

Blending of Streams

As noted previously, it may be desirable to blend an industrial waste stream with one or more further streams in order to improve efficiency, alcohol production and/or overall carbon capture of the fermentation reaction. Without wishing to be bound by theory, in some embodiments of the present invention, carboxydotrophic bacteria convert CO to ethanol according to the following:

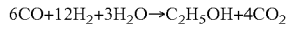

$$6CO + 12H_2 + 3H_2O \rightarrow C_2H_5OH + 4CO_2$$

However, in the presence of H2, the overall conversion is as follows:

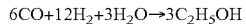

$$6CO + 12H_2 + 3H_2O \rightarrow 3C_2H_5OH$$

Accordingly, where industrial streams have a high CO content, but include minimal or no H2, it may be desirable to blend one or more streams comprising H2 with the waste stream comprising CO, prior to providing the blended substrate stream to the fermenter. The overall efficiency, alcohol productivity and/or overall carbon capture of the fermentation will be dependent on the stoichiometry of the CO and H2 in the blended stream. However, in particular embodiments the blended stream may substantially comprise CO and H2 in the following molar ratios: 20:1, 10:1, 5:1, 3:1, 2:1, 1:1 or 1:2.

In addition, it may be desirable to provide CO and H2 in particular ratios at different stages of the fermentation. For example, substrate streams with a relatively high H2 content (such as 1:2 CO:H2) may be provided to the fermentation stage during start up and/or phases of rapid microbial growth. However, when the growth phase slows, such that the culture is maintained at a substantially steady microbial density, the CO content may be increased (such as at least 1:1 or 2:1 or higher, wherein the H2 concentration may be greater or equal to zero).

Blending of streams may also have further advantages, particularly in instances where a waste stream comprising CO is intermittent in nature. For example, an intermittent waste stream comprising CO may be blended with a substantially continuous stream comprising CO and optionally H2 and provided to the fermenter. In particular embodiments of the invention, the composition and flow rate of the substantially continuous stream may be varied in accordance with the intermittent stream in order to maintain provision of a substrate stream of substantially continuous composition and flow rate to the fermenter.

Blending of two or more streams to achieve a desirable composition may involve varying flow rates of all streams, or one or more of the streams may be maintained constant while other stream(s) are varied in order to 'trim' or optimise the substrate stream to the desired composition. For streams that are processed continuously, little or no further treatment (such as buffering) may be necessary and the stream can be provided to the fermenter directly. However, it may be necessary to provide buffer storage for streams where one or more is available intermittently, and/or where streams are available continuously, but are used and/or produced at variable rates.

Those skilled in the art will appreciate it will be necessary to monitor the composition and flow rates of the streams prior to blending. Control of the composition of the blended stream can be achieved by varying the proportions of the constituent streams to achieve a target or desirable composition. For example, a base load gas stream may be predominantly CO, and a secondary gas stream comprising a high concentration of H2 may be blended to achieve a specified H2:CO ratio. The composition and flow rate of the blended stream can be monitored by any means known in the art. The flow rate of the blended stream can be controlled independently of the blending operation; however the rates at which the individual constituent streams can be drawn must be controlled within limits. For example, a stream produced intermittently, drawn continuously from buffer storage, must be drawn at a rate such that buffer storage capacity is neither depleted nor filled to capacity.

At the point of blending, the individual constituent gases will enter a mixing chamber, which will typically be a small vessel, or a section of pipe. In such cases, the vessel or pipe may be provided with static mixing devices, such as baffles, arranged to promote turbulence and rapid homogenisation of the individual components.

Buffer storage of the blended stream can also be provided if necessary, in order to maintain provision of a substantially continuous substrate stream to the bioreactor.

A processor adapted to monitor the composition and flow rates of the constituent streams and control the blending of the streams in appropriate proportions, to achieve the required or desirable blend may optionally be incorporated into the system. For example, particular components may be provided in an as required or an as available manner in order to optimise the efficiency of alcohol productivity and/or overall carbon capture.

It may not be possible or cost effective to provide CO and H2 at a particular ratio all the time. As such, a system adapted to blend two or more streams as described above may be adapted to optimise the ratio with the available resources. For example, in instances where an inadequate supply of H2 is available, the system may include means to divert excess CO away from the system in order to provide an optimised stream and achieve improved efficiency in alcohol production and/or overall carbon capture. In certain embodiments of the invention, the system is adapted to continuously monitor the flow rates and compositions of at least two streams and combine them to produce a single blended substrate stream of optimal composition, and means for passing the optimised substrate stream to the fermenter. In particular embodiments employing carboxydotrophic microbes to produce alcohol, the optimum composition of the substrate stream comprises at least 0% H2 and up to about 1:2 CO:H2.

By way of non limiting example, particular embodiments of the invention involve the utilisation of converter gas from the decarburisation of steel as a source of CO. Typically, such streams contain little or no H2, therefore it may be desirable to combine the stream comprising CO with a stream comprising H2 in order to achieve a more desirable CO:H2 ratio. H2 is often produced in large quantities at a steel mill in the coke oven. Accordingly, a waste stream from the coke oven comprising H2 can be blended with a converter waste stream comprising CO to achieve a desirable composition.

Additionally, or alternatively, a gasifier may be provided to produce CO and H2 from a variety of sources. The stream produced by the gasifier may be blended with a stream comprising CO to achieve a desirable composition. Those skilled in the art will appreciate that gasifier conditions can be controlled to achieve a particular CO:H2 ratio. Furthermore, the gasifier may be ramped up and down to increase and decrease the flow rate of the stream comprising CO and H2 produced by the gasifier. Accordingly, a stream from a gasifier may be blended with a substrate stream comprising CO to optimise the CO:H2 ratio in order to increase alcohol productivity and/or overall carbon capture. Furthermore, the gasifier may be ramped up and down to provide a stream of varying flow and/or composition that may be blended with an intermittent stream comprising CO to achieve a substantially continuous stream of desirable composition.

Other sources of CO and/or H2 that may be blended with a substrate stream comprising CO include reformation of hydrocarbons, such as natural gas and/or methane and reformation of methanol.

Addition of Scrubber Water

In accordance with the invention, scrubber water is utilised in the fermentation reaction to increase the efficiency of growth and product production.

The scrubber water may be from any appropriate industrial source, as described hereinbefore. In a particular embodiment of the invention, the scrubber water is obtained from the process of cleaning one or more exhaust gases generated during steel manufacture. By way of example, the scrubber water is obtained from cleaning off gases from coking ovens, the blast furnace, the basic oxygen furnace, and/or the electric arc furnace.

In certain embodiments, the scrubber water is sourced from the same industrial process from which the (gaseous) fermentation substrate is sourced; for example, both the scrubber water and substrate (CO containing exhaust gases) are derived from the same steel mill.

The scrubber water may be used in raw form direct from the scrubbing system or apparatus of the industrial process. However, the scrubber water may be processed to remove or at least reduce the level of residual particulate matter therein. Methods for processing the scrubber water will be appreciated by those of skill in the art to which the invention relates.

However, by way of example, the scrubber water may be filtered, centrifuged or allowed to settle prior to introduction into the fermenter.

As discussed above, the pH of the scrubber water may be adjusted prior to use. The appropriate pH will be dependent on the conditions required for a particular fermentation reaction having regard to the nutrient media and micro-organisms used, as will be appreciated by persons of ordinary skill in the art to which the invention relates. In one preferred embodiment, in fermentation of a gaseous substrate containing CO utilising *Clostridium autoethanogenum* the pH may be adjusted to approximately 5.5 to 6.5, most preferably approximately 5.5. Further examples include, pH 5.5 to 6.5 using *Moorella thermoacetica* for the production of acetic acid, pH 4.5 to 6.5 using *Clostridium acetobutylicum* for the production of butanol and pH 7 using *Carboxydothermus hygrogenaformans* for the production of hydrogen.

The scrubber water may be added to the fermentation reaction using any appropriate means. By way of example, it may be directly fed from a scrubbing apparatus into a bioreactor in which fermentation is occurring or is to occur. Alternatively, it may be collected from a scrubbing apparatus and stored in an appropriate chamber which feeds the bioreactor, or it may be collected from a scrubbing apparatus, stored and manually fed into the bioreactor. Addition of the scrubber water to the bioreactor can be continuous, or the scrubber water can be added at certain time points in the fermentation reaction, or on demand, as circumstances require.

In one embodiment of the invention, the scrubber water is mixed with nutrient media to be used in the fermentation reaction and then added to the bioreactor by any one of the foregoing means. Accordingly, the invention also provides a composition comprising a mixture of an appropriate nutrient media and scrubber water. Persons of ordinary skill in the art to which the invention relates will appreciate appropriate nutrient media for use in microbial fermentation. However, by way of example, such media may contain sources of nitrogen, phosphate, potassium, sodium, sulphur, a range of metal ions and B vitamins, and the like. An exemplary media is provided herein after in the section entitled "Examples".

The scrubber water may be used in an amount of up to approximately 1:9 nutrient media to scrubber water. In one preferred embodiment of the invention, the scrubber water is used at a ratio of approximately 1:1 nutrient media to scrubber water.

As will be appreciated, the scrubber water resulting from particular processes may contain components that are toxic or harmful to particular micro-organisms. Thus, the invention does not exclude all pre-treatment processes but avoids such additional processes if possible. Alternatively or in addition, the ratio of the content of scrubber water in a bioreactor may be controlled such that potentially toxic or harmful components are maintained below acceptable concentrations.

Scrubber Water as Primary Feedstock

In another embodiment of the invention, the fermentation reaction is conducted using only scrubber water as the feedstock. In other words, the scrubber water is the primary source of carbon for the fermentation reaction. In this embodiment, the fermentation reaction may be carried out substantially as hereinbefore described, but it is not necessary to provide or capture CO containing gases or provide an alternative carbon source.

Scrubber water may be fed to a bioreactor in which fermentation will occur as described hereinbefore. In one embodiment, it is fed directly and continuously to a bioreactor from a scrubbing system or apparatus at an appropriate level to maintain optimal conditions for the fermentation reaction.

In a related embodiment, the scrubber water is stored and then fed to the bioreactor at times when an alternative feedstock or substrate is unavailable. For example, exhaust gases generated in certain steel manufacturing processes are not constant but intermittent. When these gases are unavailable to feed the fermentation reaction, scrubber water is fed to the bioreactor to maintain alcohol production and increase the overall efficiency of the reaction. Such a process, whereby scrubber water is supplemented with fermentation media and fed to a bioreactor, can be conducted in using a cell retention system (e.g. cross flow membrane filtration, continuous centrifugation or an immobilised cell system). In this embodiment, the mixture of scrubber water and fermentation media can flow through the reactor, providing nutrition to the bacteria. An advantage of this system is that the scrubber water contains high levels of dissolved carbon monoxide. Because a major process operating cost associated with the use of gaseous substrates for fermentation is the purchase and operation of equipment to allow CO gas mass-transfer from the gas phase to the liquid phase, the use of liquid streams that already contain CO will significantly reduce this cost.

General

Embodiments of the invention are described by way of example. However, it should be appreciated that particular steps or stages necessary in one embodiment may not be necessary in another. Conversely, steps or stages included in the description of a particular embodiment can be optionally advantageously utilised in embodiments where they are not specifically mentioned.

While the invention is broadly described with reference to any type of stream that may be moved through or around the system(s) by any known transfer means, in certain embodiments, the substrate and/or exhaust streams are gaseous. Those skilled in the art will appreciate that particular stages may be coupled by suitable conduit means or the like, configurable to receive or pass streams throughout a system. A pump or compressor may be provided to facilitate delivery of the streams to particular stages.

Furthermore, a compressor can be used to increase the pressure of gas provided to one or more stages, for example the bioreactor. As discussed hereinabove, the pressure of gases within a bioreactor can affect the efficiency of the fermentation reaction performed therein. Thus, the pressure can be adjusted to improve the efficiency of the fermentation. Suitable pressures for common reactions are known in the art.

In addition, the systems or processes of the invention may optionally include means for regulating and/or controlling other parameters to improve overall efficiency of the process. One or more processors may be incorporated into the system to regulate and/or control particular parameters of the process. For example particular embodiments may include determining means to monitor the composition of substrate and/or exhaust stream(s). In addition, particular embodiments may include a means for controlling the delivery of substrate stream(s) to particular stages or elements within a particular system if the determining means determines the stream has a composition suitable for a particular stage. For example, in instances where a gaseous substrate stream contains low levels of CO or high levels of O2 that may be detrimental to a fermentation reaction, the substrate stream may be diverted away from the bioreactor. In particular embodiments of the invention, the system includes means for monitoring and controlling the destination of a substrate stream and/or the flow rate, such that a stream with a desired or suitable composition can be delivered to a particular stage.

In addition, it may be necessary to heat or cool particular system components or substrate stream(s) prior to or during one or more stages in the process. In such instances, known heating or cooling means may be used. For example, heat exchangers may be employed to heat or cool the substrate streams.

Furthermore, the system may include one or more pre/post treatment steps to improve the operation or efficiency of a particular stage. For example, a pre-treatment step may include means for removing particulate matter and/or long chain hydrocarbons or tars from a gaseous substrate stream. Other pre- or post-operations that may be conducted include separation of desired product(s) from particular stages, such as, for example, the bioreactor production stage (e.g. removal of ethanol by distillation).

Various embodiments of systems of the invention are described in the accompanying Figures. The alternative embodiments described in FIGS. 1-13 comprise features in common with one another and the same reference numbers have been used to denote the same or similar features in the various figures. Only the new features (relative to FIG. 1) of FIGS. 2 to 13 are described, and so these Figures should be considered in conjunction with the description of FIG. 1.

FIG. 1 is a schematic representation of a system 101 according to one embodiment of the invention. Input substrate stream 1 enters system 101 via a suitable conduit. Input substrate stream 1 comprises CO and optionally $CO_2$ and, in certain embodiments, the substrate stream is a waste gas stream from an industrial process, such as that released during the carburisation of steel in a basic oxygen furnace. The levels of components within gas stream 1 may fluctuate. Optional valve 2 may be included to divert stream 1 elsewhere (indicated by stream 3) if it is determined that stream 1 does not have a desired composition. For example, where it is desirable to obtain CO from stream 1, a minimum CO content may be set for stream 1, whereby the stream is diverted away from further processing in system 101 if the minimum CO content is not met. Such a threshold may be set to avoid uneconomic or non-viable processing of a stream. Any known means may be used to determine whether a gas has a desirable composition. Also, "desirable composition" refers not only to substances desired to be included in stream 1, but also to undesired components. For example, stream 1 may be diverted if a particular contaminant is present in stream 1.

As will be appreciated by one of skill in the art, valve 2 may be positioned elsewhere within system 101. For example, it may be placed after processing by bioreactor 5.

If a determination is made that stream 1 has a desired composition, it is passed to optional pre-treat 4. Pre-treat 4 may be used to control various aspects of the stream, including temperature and levels of contaminants or other undesired components or constituents. It may also be used to add components to the stream. This will depend on the particular source of gas stream 1 and/or the particular fermentation reaction and/or the micro-organisms selected therefor.

Pre-treat 4 may be positioned elsewhere within system 101 or may be omitted, or multiple pre-treats 4 may be provided at various points in system 101. This will depend on the particular source of gas stream 1 and/or the particular fermentation reaction and/or the micro-organisms selected therefor. For example, additional pre-treat(s) may be provided upstream of $CO_2$ remover 8 to control aspects of the stream entering the $CO_2$ remover 8.

Following optional pre-treatment the stream may be passed to bioreactor 5 by any known transfer means. For example, the stream may be driven through the system with one or more fans and/or pumps. Bioreactor 5 is configured to perform the desired fermentation reaction to produce products. According to certain embodiments, bioreactor 5 is configured to process a CO containing substrate so as to produce one or more acids and/or one or more alcohols. In a particular embodiment, bioreactor 5 is used to produce ethanol and/or butanol. Bioreactor 5 may comprise more than one tank, each tank being configured to perform the same reaction and/or different stages within a particular fermentation process and/or different reactions, including different reactions for different fermentation processes which may include one or more common stages.

Bioreactor 5 may be provided with cooling means for controlling the temperature therein within acceptable limits for the micro-organisms used in the particular fermentation reaction to be performed.

The products produced in the bioreactor 5 may be recovered by any recovery process known in the art. However, in some embodiments of the invention, at least a portion of the product may exit the bioreactor 5 in a stream 7, comprising components such as $CO_2$ and optionally unconverted CO. Such streams can be optionally treated in product remover 6 to remove any product before the substantially product free stream 7 is passed to $CO_2$ remover 8.

$CO_2$ remover 8 is configured to receive stream 7, wherein at least a portion of $CO_2$ present in stream 7 is removed therefrom, leaving a remaining waste stream 9. In certain embodiments, the $CO_2$ remover 8 is configured to separate at least a portion of the $CO_2$ component from the stream 7 and is adapted to capture the separated $CO_2$ and/or convert it into products suitable for further use or storage. Alternatively, the $CO_2$ remover 8 may be configured to capture $CO_2$ directly and/or convert it into products, from stream 7.

Where bioreactor 5 comprises a plurality of stages or separate tanks, streams from at least a subset of the stages may be received by $CO_2$ remover 8. Also, more than one downstream $CO_2$ remover 8 may be provided so that the same stream undergoes a plurality of $CO_2$ removal steps, or the same or a different removal step may be performed on streams from different fermentation stages or tanks.

Figure 2:
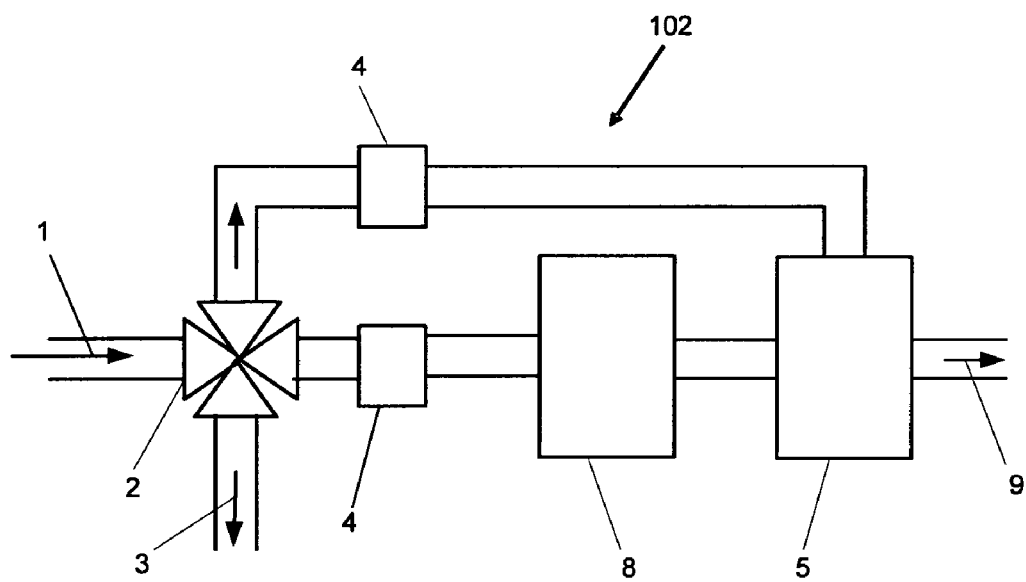
FIG. 2: is a schematic representation of a system including a CO2 remover upstream of a bioreactor according to certain embodiments of the invention.

According to an alternative embodiment represented in FIG. 2, $CO_2$ remover 8 is positioned upstream of bioreactor 5 (c.f. downstream in FIG. 1). Thus, according to the embodiment of FIG. 2, $CO_2$ remover 8 may be used to capture $CO_2$ from the substrate stream before it is passed to bioreactor 5. Optional valve 2 may be configured such that, if it is determined that the $CO_2$ content is too low for efficient and/or effective $CO_2$ capture, the stream can be passed directly to the bioreactor 5. Alternatively, stream 3 may be directed away from the system altogether, for example, in circumstances where a stream is unsuitable for $CO_2$ removal or fermentation.

Figure 3:
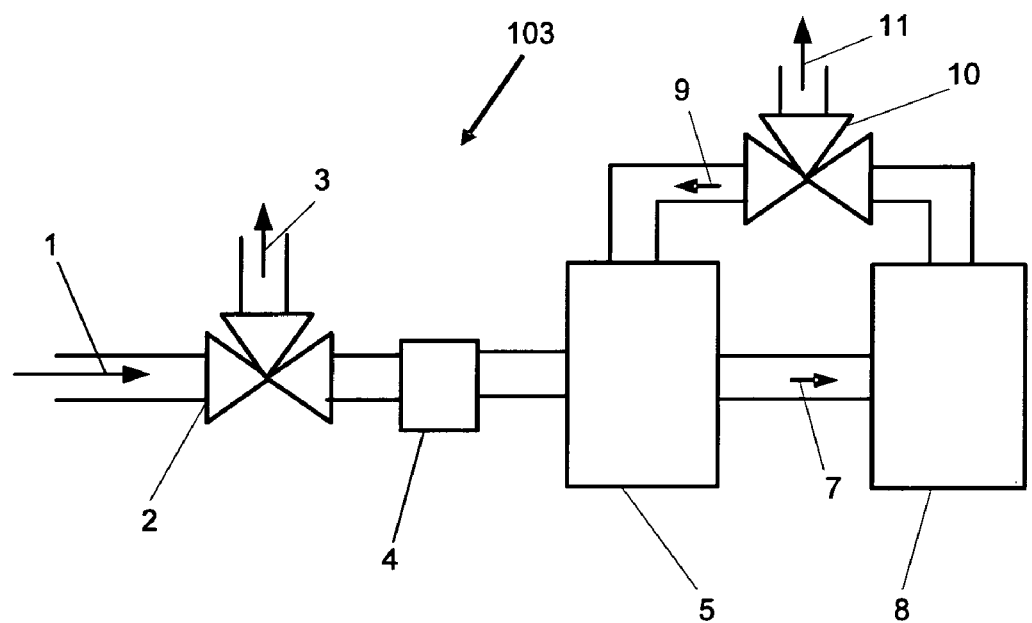
FIG. 3: is a schematic representation of a system including a CO2 remover downstream of a bioreactor and means for returning a substrate stream to the bioreactor.

According to the embodiment of FIG. 3, $CO_2$ remover 8 is provided downstream of bioreactor 5 and valve 10 is configured to direct stream 9 back into bioreactor 5 if it is determined that sufficient CO remains in stream 9 for further fermentation to products. However, if it is determined that the CO content of the stream is below a desired level, the stream can be directed elsewhere (as indicated by stream 11). The embodiment of FIG. 3 also includes the attendant advantages of both the embodiment of FIG. 1 and that of FIG. 2.

Figure 4:
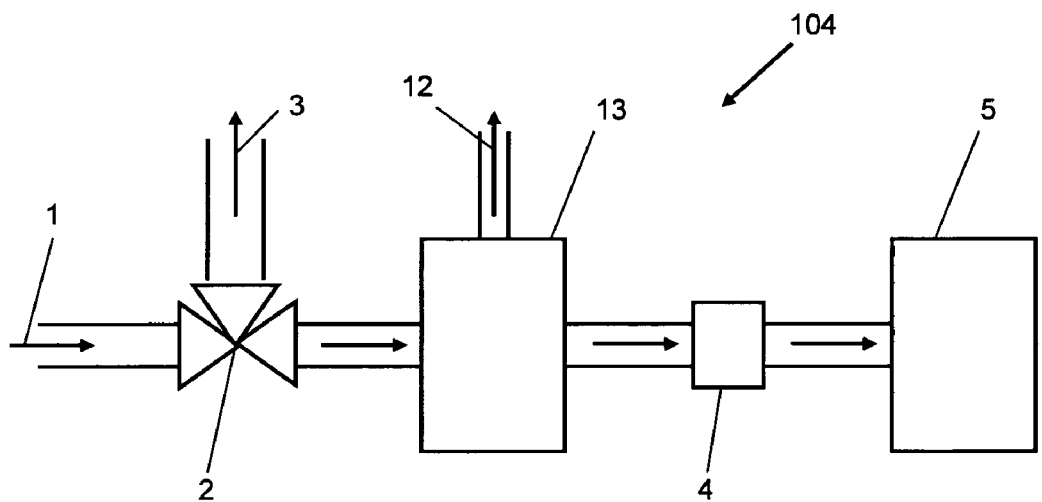
FIG. 4: is a schematic representation of a system including a gas separator upstream of a bioreactor according to certain embodiments of the invention.

FIG. 4 is a schematic representation of a system 104 according to a further embodiment of the invention. Input gas stream 1 enters system 104 via a suitable conduit. Input gas stream 1 may be a waste gas stream from an industrial process, such as that released during the carburisation of steel in a basic oxygen furnace. Input gas stream 1 preferably comprises at least one carbon-based gas. In particular embodiments, stream 1 comprises CO and/or CO2. The levels of components within gas stream 1 may fluctuate. Optional valve 2 may be included to divert stream 1 elsewhere if it is determined that stream 1 does not have a desired composition (as indicated by stream 3). For example, where it is desirable to obtain CO from stream 1, a minimum CO content may be set for stream 1, whereby the stream is diverted away from further processing in system 104 if the minimum content is not met. Such a threshold may be set to avoid uneconomic or non-viable processing of a stream. Any known means may be used to determine whether a gas has a desirable composition. As noted above, "desirable composition" may refer not only to substances desired to be included in stream 1, but also to undesired components. For example, stream 1 may be diverted if a particular contaminant is present in stream 1.

As will be appreciated by one of skill in the art upon consideration of the instant disclosure, valve 2 may be positioned elsewhere within system 104. For example, it may be placed in the system after processing by gas separator 13.

If a determination is made that stream 1 has a desired composition, it is passed to gas separator 13. At least a first component of gas stream 1 is separated therefrom, leaving a remaining component. Either the at least a first component or the remaining component may be diverted as stream 12, with the other component being passed to optional pre-treat 4 and bioreactor 5. Thus, where CO is required in a gas stream to feed a fermentation reaction, the CO may be separated from the remainder of the stream, with only the CO (or a CO-enriched stream) being passed to bioreactor 5. Alternatively, one or more components of the stream (e.g. O2 and/or H2) may be separated so that they are at least partly removed, with the remainder of the stream being passed to bioreactor 5.

As would be apparent to one of skill in the art upon consideration of the instant disclosure, gas separator 13 may comprise one or a plurality of stages or separate units, with one or more gases being separated at each stage.

Further description of processes and arrangements for gas separation are provided hereinbelow.

As noted above, pre-treat 4 may be positioned elsewhere within system 104 or may be omitted, or multiple pre-treats 4 may be provided at various points in system 104. Use of pre-treat 4 may depend on the particular source of gas stream 1 and/or the particular fermentation reaction and/or the micro-organisms selected therefor.

Bioreactor 5 is configured to perform the desired fermentation reaction. According to certain embodiments, bioreactor 5 is configured to process a CO containing substrate so as to produce one or more acids and/or one or more alcohols. In particular embodiments, bioreactor 5 is used to produce ethanol and/or butanol. Bioreactor 5 may comprise more than one tank, each tank being configured to perform the same reaction and/or different stages within a particular fermentation process and/or different reactions, including different reactions for different fermentation processes which may include one or more common stages.

Bioreactor 5 may be provided with cooling means for controlling the temperature therein within acceptable limits for the micro-organisms used in the particular fermentation reaction to be performed.

Figure 5:
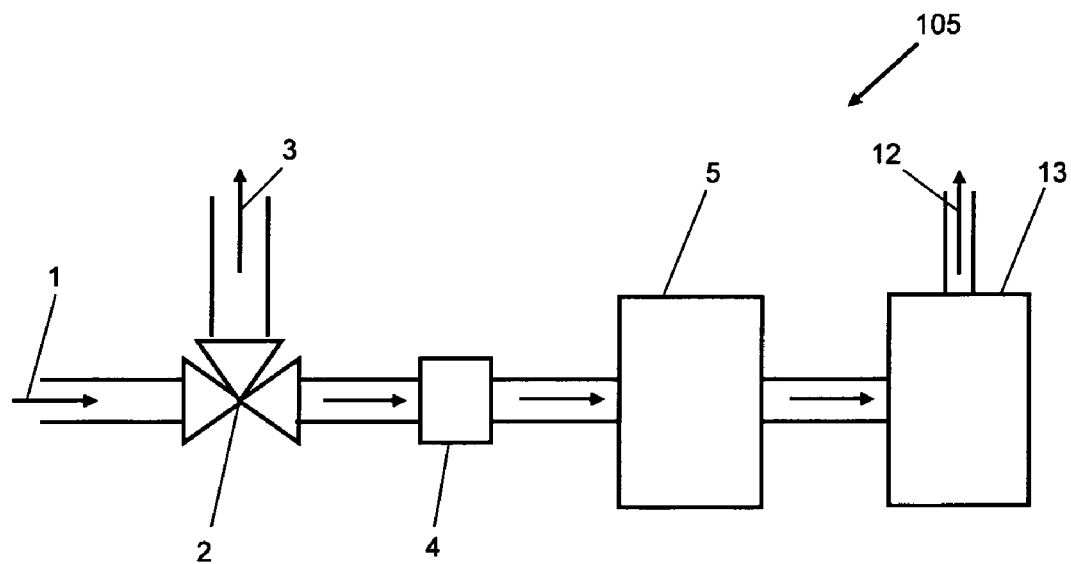
FIG. 5: is a schematic representation of a system including a gas separator downstream of a bioreactor according to certain embodiments of the invention.

According to the alternative embodiment of FIG. 5, gas separator 13 is positioned downstream of bioreactor 5 (c.f. upstream in FIG. 4). Thus, according to the embodiment of FIG. 5, gas separator 13 may be used to separate one or more components of gases produced by the fermentation reaction in bioreactor 5, and/or separate gases that have been fed to but not used in bioreactor 5. Where bioreactor 5 comprises a plurality of stages or separate tanks, gases from at least a subset of the stages may be received by gas separator 13. Also, more than one downstream gas separator 13 may be provided, so that the same gas stream undergoes a plurality of separations, or the same or a different separation may be performed on gas streams from different fermentation stages or tanks.

Figure 6:
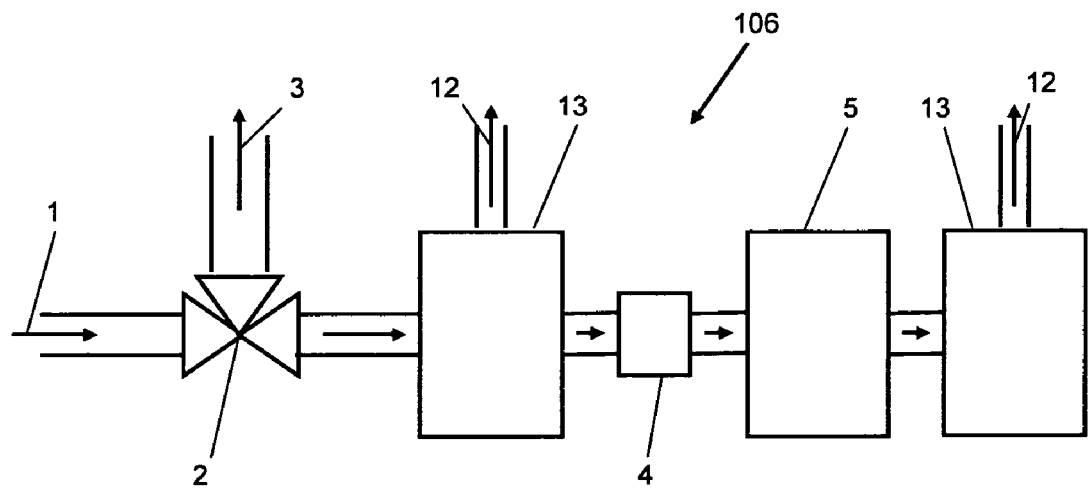
FIG. 6: is a schematic representation of a system including two gas separators: one gas separator upstream of a bioreactor and one gas separator downstream of a bioreactor according to certain embodiments of the invention.

According to the embodiment of FIG. 6, gas separators 13 are provided upstream and downstream of bioreactor 5 with the attendant advantages of both the embodiment of FIG. 4 and FIG. 5.

A pump or compressor (not shown) may be provided upstream of bioreactor 5 so that the pressure of gas within bioreactor 5 is increased. As discussed hereinabove, the pressure of gases within a bioreactor can affect the efficiency of the fermentation reaction performed therein. Thus, the pressure can be adjusted to improve the efficiency of the fermentation. Suitable pressures for common reactions are known in the art.

Gas stream 1 may comprise a plurality of different streams. Separate processing elements may be provided for different streams, with only a subset of the elements being common. For example, a first stream may be received by a first gas separator and a second stream may be received by a second separator. Outputs from both the first and second separators may then be passed to a common bioreactor. Other levels of commonality or difference are included within the scope of the invention.

Figure 7:
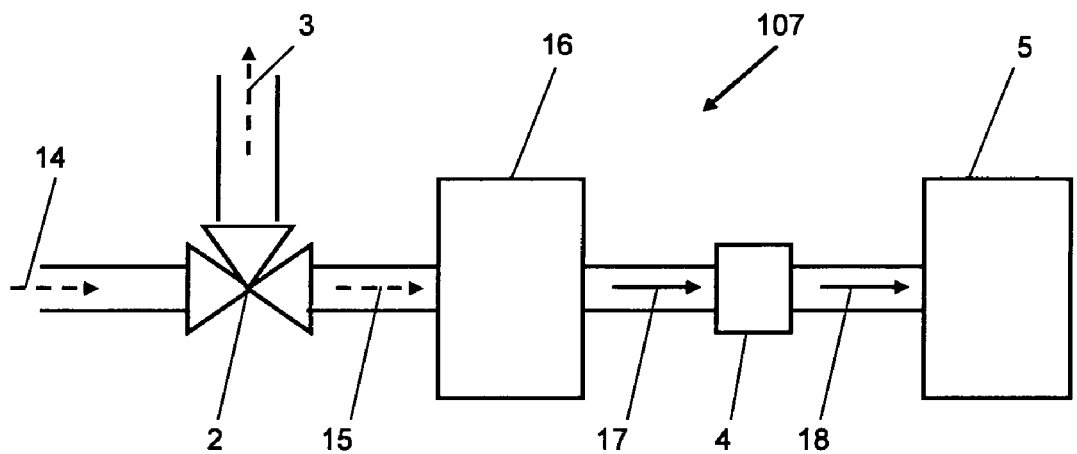
FIG. 7: is a schematic representation of a system including a buffer storage tank according to certain embodiments of the invention.

FIG. 7 is a schematic representation of a system 107 according to one embodiment of the invention. Waste gas stream 14 enters system 107 via a suitable conduit from an industrial process (e.g. carburisation of steel in a BOF). Stream 14 is intermittent in nature as indicated by the broken line. Stream 14 may be a constant stream in the sense that it is constantly supplied, but the content of particular gases within the stream may vary over time. For example, CO within stream 14 may vary between high and low levels over time. Regardless of whether stream 14 is in fact constantly or intermittently produced, during times when the levels of a desired gas are too low to support a fermentation reaction (or levels of an unwanted gas (e.g. O2) are too high), valve 2 may be used to divert the stream 14 elsewhere, including into the atmosphere (as indicated by stream 3). At times when stream 14 comprises a desired gas at a desired concentration, valve 2 passes resultant stream 15 to buffer storage tank 16. Stream 15 is also shown in broken line due to its possibly intermittent nature.

Buffer storage tank 16 acts as a reservoir which feeds gas to bioreactor 5 after any pre-treatment of the gas at pre-treat 4. Pre-treat 4 may be positioned elsewhere within system 1 or even omitted, depending on the particular source of gas stream 14 and/or the particular fermentation reaction and/or the micro-organisms selected therefor.

Buffer storage tank 16 preferably releases a steady stream 17 of gas, which is passed to pre-treat 4 and then to bioreactor 5 as steady stream 18. Streams 17 and 18 are shown as a continuous line to reflect their substantially continuous nature. Gas may be compressed within buffer storage tank 16 to reduce the space required therefor. A valve (not shown) or other means may be used to set the rate of flow of gas from buffer storage tank 16. The rate is preferably constant and selected such that buffer storage tank 16 always has a supply of gas and does not become depleted. According to one embodiment, control means (not shown) may control the valve to vary the rate of flow of gas 15 depending on the amount of gas contained therein. More particularly, when the gas stored in buffer storage tank 16 falls below a predetermined level, the rate of flow of gas from buffer storage tank 16 may be reduced so that, while optimal levels of gas are not passed to bioreactor 5, reduced levels are provided which may at least mitigate the effects on the productivity of bioreactor 5 by providing improved conditions for the micro-organisms inside bioreactor 5.

Thus, the intermittent nature of stream 14 is mitigated in the embodiment shown in FIG. 7 due to buffering of gas in storage tank 16.

As would be apparent to one of skill in the art upon consideration of the instant disclosure, buffer storage tank 16 preferably includes an exhaust port for removing waste gases of the fermentation process. Bioreactor 5 may also be provided with cooling means for controlling the temperature therein within acceptable limits for the micro-organisms.

According to an alternative embodiment of system 107, buffer storage tank 16 is substituted by an alternative form of storage that performs the same or a similar function. These may include one or more of absorption, adsorption, and pressure and/or temperature swings. According to one embodiment, the gas is stored in solution with the solution then being fed to bioreactor 5. Such an arrangement may reduce the processing time within bioreactor 5, because the required gases are already dissolved before they reach the bioreactor 5.

Figure 8:
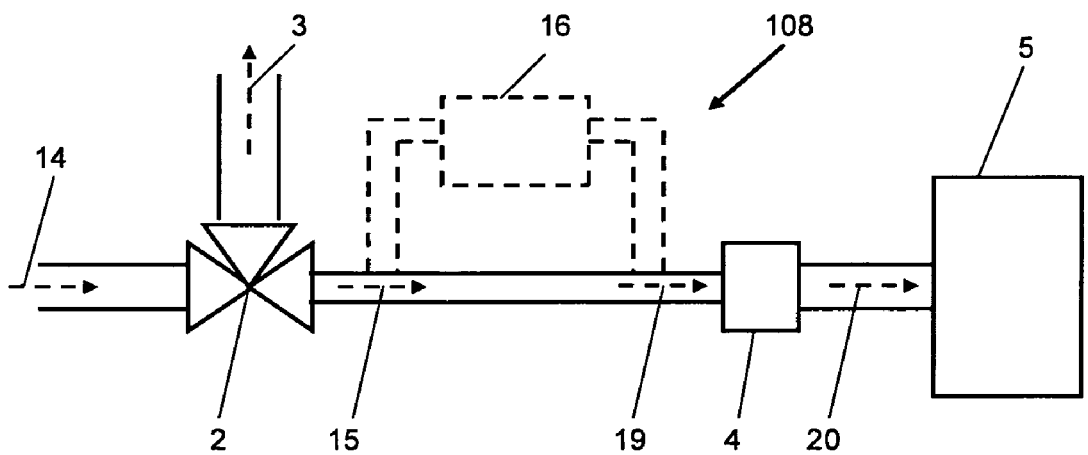
FIG. 8: is a schematic representation of a system including an optional buffer storage tank according to certain embodiments of the invention.

In the arrangement shown in FIG. 8, buffer storage tank 16 is optional, as indicated by the broken line. In embodiments omitting buffer storage tank 16, stream 14 is passed to bioreactor 5 as and when available and having an acceptable composition, resulting in streams 19 and 20 being intermittent in nature. As aforementioned, this may not be ideal for particular micro-organisms or processes. Where buffer storage tank 16 is included, a portion of stream 15 may be diverted thereto so that when stream 15 is available, gas is passed both to bioreactor 5 and buffer storage tank 16. Gas passed to buffer storage tank 16 may be stored until such times when stream 15 is not available. At least a low level stream of gas may then be passed from buffer storage tank 16 to bioreactor 5.

As would be apparent to one of skill in the art, waste gas stream 14 from an industrial process may be at a high temperature. Allowable temperature ranges for micro-organisms vary but are of the order of 30° C. to 50° C. for anaerobic bacteria typically used to produce alcohols such as ethanol. Gas stream 14 can cause the temperature within bioreactor 5 to rise, which is exacerbated by the exothermic nature of the fermentation processes, resulting in a need for cooling measures to be included within the system. According to one embodiment, the intermittent nature of stream 14 is taken into account when configuring the cooling means for bioreactor 5. More particularly, during times when stream 14 is not available or not of the desired composition, the temperature inside bioreactor 5 may be reduced to that of the lower end of the allowable temperature range for the micro-organisms used (e.g. towards 30° C.). Then, when gas stream 14 is available with the desired composition, a temperature rise inside bioreactor 5 is allowed, thereby reducing the requirements of the cooling means that are provided when gas is fed to bioreactor 5. Thus, for anaerobic bacteria typically used to produce alcohols such as ethanol, the temperature inside bioreactor 5 may be allowed to approach 50° C. According to one embodiment, in the event of bioreactor 5 approaching a maximum allowable temperature, gas stream 14 may be inhibited from entering bioreactor 5 even if it is available at the desired composition, so as to enable the temperature within bioreactor 5 to be more readily controlled. In such cases, the gas may be stored for later use or diverted elsewhere, where it may undergo additional processing steps as would be apparent to one of skill in the art upon consideration of the instant disclosure. Particular embodiments of the invention provide for levelling of the cooling load.

Figure 9:
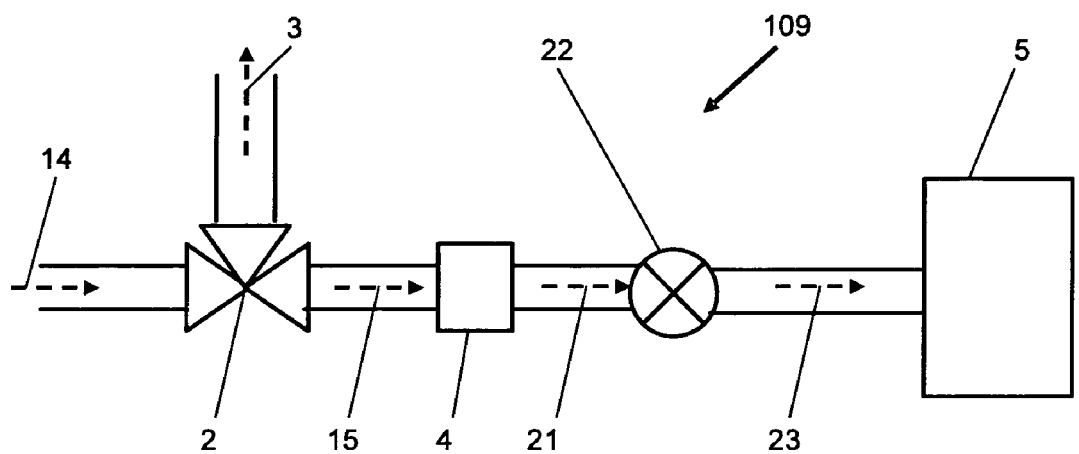
FIG. 9: is a schematic representation of a system including a compressor according to certain embodiments of the invention.

FIG. 9 is a schematic representation of a system 109 according to another embodiment of the invention. Compressor 22 serves to compress intermittent stream 21, when available, delivering compressed stream 23 to bioreactor 5. Thus, according to the embodiment of FIG. 9, bioreactor 5 effectively functions as both a fermentation tank and a storage tank by holding gas therein at an elevated pressure when stream 14 is available and has the desired composition. During breaks in stream 14 or when stream 14 does not have the desired composition, waste gases may be slowly exhausted from bioreactor 5 such that the pressure of gas within bioreactor 5 drops, but such that sufficient levels of any desired gases are continuously maintained or sufficiently well maintained to avoid significant periods of time during which the micro-organisms are deprived of the gases.

Figure 10A:
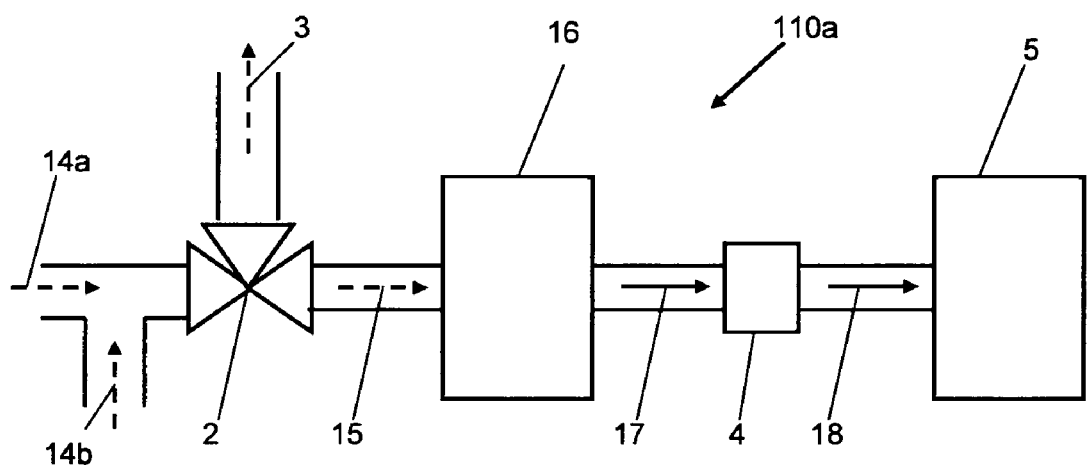
FIG. 10a: is a schematic representation of a system including multiple substrate stream sources and a buffer storage tank according to certain embodiments of the invention.
Figure 10B:
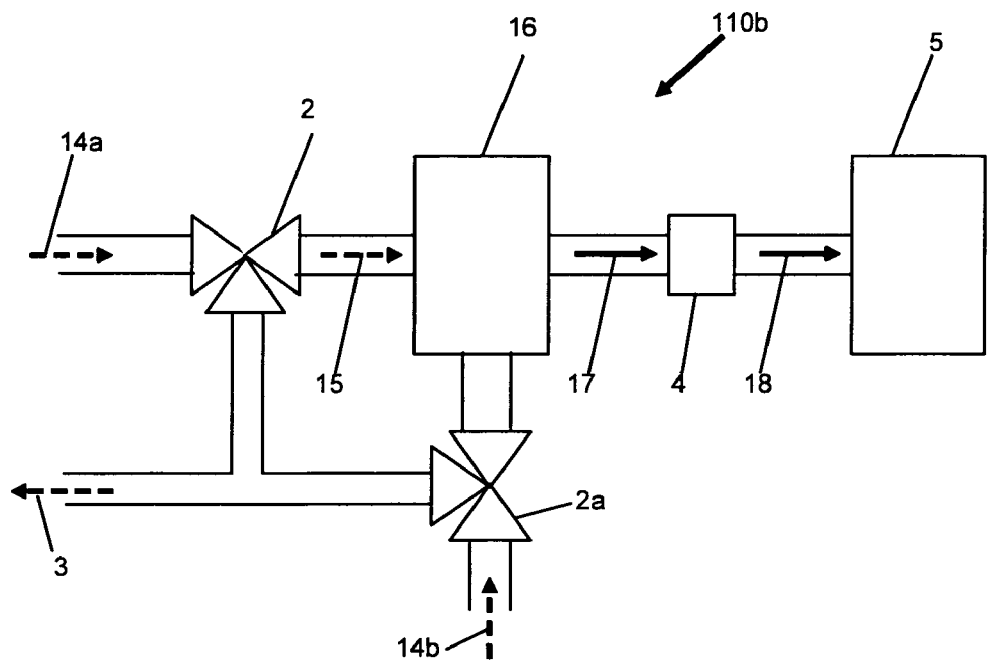
FIG. 10b: is a schematic representation of a system including multiple substrate stream sources and a buffer storage tank according to certain embodiments of the invention.

FIGS. 10a and 10b are schematic representations of systems 110a and 110b according to another embodiment of the invention in which multiple intermittent gas streams 14a and 14b are used to feed the fermentation reaction within bioreactor 5. Thus, when stream 14a is unavailable or does not have the desired composition, bioreactor 5 may alternatively be fed by stream 14b. As would be apparent to one of skill in the art, more than two gas stream sources may be available. Also, the amount of commonality between processing steps of the streams may vary depending on particular compositions of each stream. The arrangement shown in FIGS. 10a and 10b may be implemented in a steel mill with different streams originating from different stages in the steel making process. Additionally or alternatively, other gas sources may be used. For example, in fermentations using anaerobic bacteria to produce alcohols such as ethanol, conventional sources may be used to provide the stream (e.g. biomass).

Figure 11:
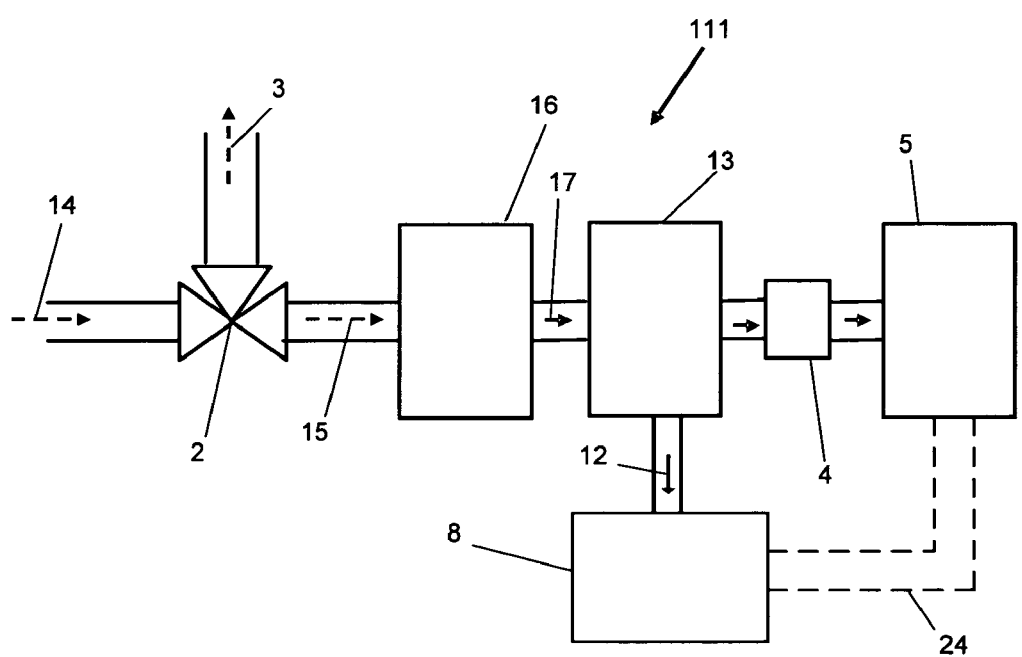
FIG. 11: is a schematic representation of a system including a buffer storage tank, gas separator and CO2 remover according to certain embodiments of the invention.

FIG. 11 is a schematic representation of a system 111 according to another embodiment of the invention, incorporating several of the stages previously described herein. Intermittent stream 14 is converted into a substantially continuous stream 17 as previously described with reference to FIG. 7. Substantially continuous stream 17 is passed to gas separator 13, which is adapted to separate CO2 from other components of the substrate stream, such as CO. The separated stream 12 comprising CO2, is passed to CO2 remover 8, where it can be converted into products suitable for further use or stored. The remainder of the stream comprising CO is passed to optional pre-treat 4 and then on to bioreactor 5. Optional conduit 24 may be provided to pass a stream comprising CO2 exiting the bioreactor 5 back to CO2 remover 8, where it can be converted into products suitable for further use or stored.

Figure 12:
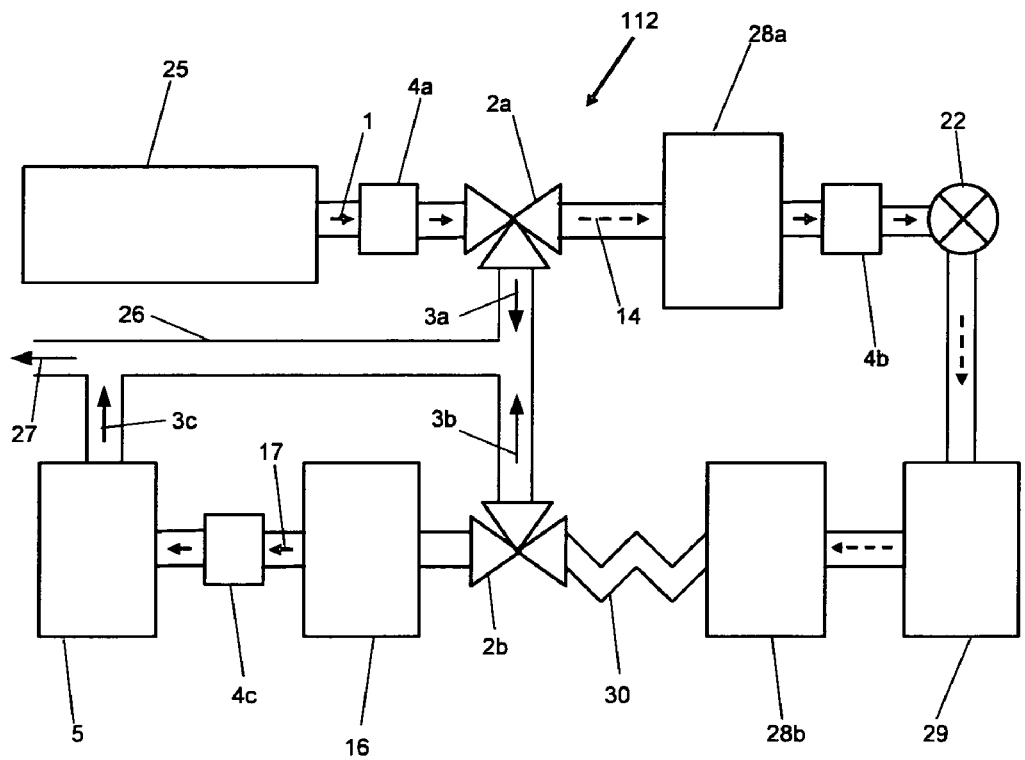
FIG. 12: is a schematic representation of a system adapted to capture carbon from a waste stream according to certain embodiments of the invention.

FIG. 12 is a schematic representation of a system 112 according to a further embodiment of the invention. Blown oxygen furnace 25 may be part of an industrial process such as the decarburisation of steel and produces waste stream 1. In particular embodiments, waste stream 1 comprises CO and/or CO2. Waste stream 1 is passed through optional pre-treat 4a. Typically pre-treat 4a will be a scrubber or water bath adapted to remove particulate matter from stream 1. Valve 2a is adapted to divert at least a portion of stream 1 into waste stack 26 when it is determined the stream does not have the desired composition. The diverted stream is represented by arrow 3a. Typically the stream diverted into the waste stack 26 will exit into the atmosphere as represented by arrow 27. Typically, the stream is gaseous and can be driven into the waste stack and optionally throughout the system 113 by one or more fans and/or pumps.

If it is determined that stream 1 has a desired composition, it can be diverted to optional heat exchanger 28a as stream 14. Typically, stream 14 will be intermittent in nature and may need cooling. Heat exchanger 28a may be any heat exchanging means known in the art. However, by way of example, it is a shell tube heat exchanger. Optional pre-treat 4b may be used to remove residual particulate matter from the stream if necessary. By way of example, a membrane filter can be used to remove residual particulate matter from the stream. Pre-treat 4b may also include means to remove condensed water from the optionally cooled stream, such as a knock-out pot or other suitable moisture collection means known in the art.

The stream can be pressurised by any suitable means, such as gas compressor 22, before passing to oxygen removal stage 29. Any means suitable for removal of oxygen may be used, however by way of example; oxygen removal stage 29 includes a hot copper catalyst or a catalytic converter. The stream can be cooled using optional heat exchanger 28b, before passing into holding tube 30. Holding tube 30 is of sufficient length such that the composition of the stream can be determined by any appropriate determining means (not shown) before the stream reaches valve 2b. If it is determined that the stream has a desirable composition it can be diverted to buffer storage means 16 by valve 2b. If the composition is not suitable for fermentation, for example the oxygen content is too high, valve 2b can divert the stream into waste stack 26 (as represented by arrow 3b). Buffering means 16 passes substantially continuous substrate stream 17 to the bioreactor 5, via optional pre-treat 4c. Optional pre-treat 4c can be used to remove unwanted contaminants such as microbes from stream 17. By way of example, a sterilisation filter or membrane can be used to remove unwanted bacteria from the stream. Waste stream 3c exiting the bioreactor 5 can also be passed to waste stack 26.

Means for determining the composition of the stream may be optionally included at any stage of the system. By way of example means for determining the O2, CO and/or CO2 composition can be included upstream of valve 2a, upstream of holding tube 30 or valve 2b and/or upstream of bioreactor 5. Furthermore, due to the potentially flammable nature of the streams, safety equipment such as flame arresters can also be included at any stage of the system.

Figure 13:
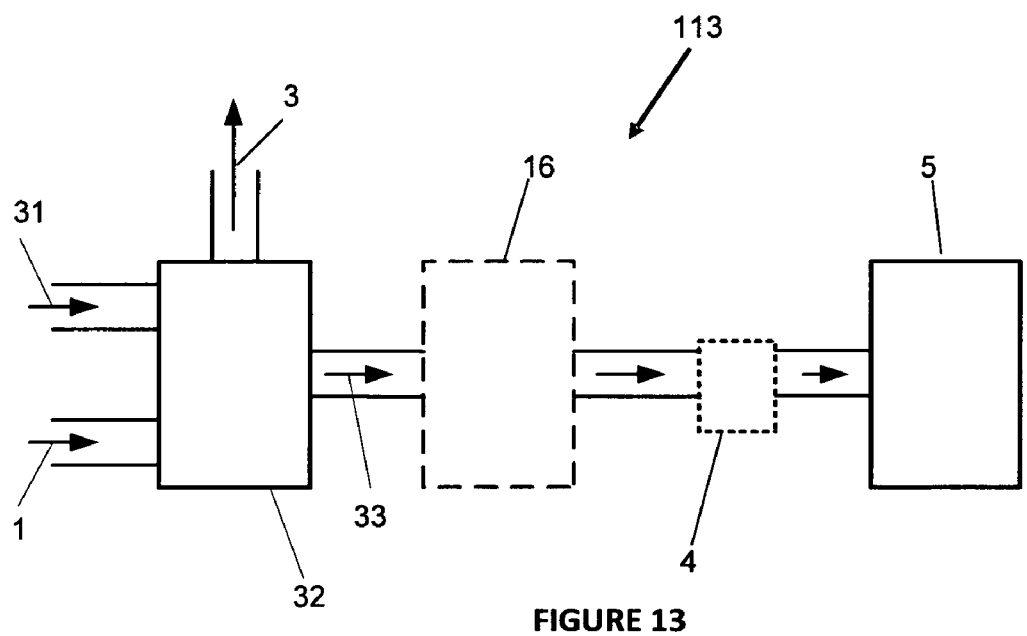
FIG. 13: is a schematic representation of a system including a blending means, according to certain embodiments of the invention.

FIG. 13 is a schematic representation of a system 113 according to a further embodiment of the invention. Waste stream 1 and stream 31, either or both of which may be intermittent in nature, are directed into blender 32. Blender 32 is adapted to control the flow of at least two streams (such as stream 1 and 31) and mix the streams to achieve a stream with a desired composition (stream 33). Unwanted streams, such as streams with an undesirable composition may be diverted away from the system 113 as indicated by arrow 3, while streams with a desirable composition 33, may be directed to optional buffer 16, optional pretreat 4 then bioreactor 5 for conversion to products. The composition and flow rates of streams 1, 3, 31 and 33 may be monitored continuously or otherwise by any means known in the art.

Stream 1 and/or stream 31 may additionally or alternatively be diverted away from blender 32 before entry therein based on their individual compositions. Such an arrangement enables one of streams 1, 31 to be used where only one has an undesirable composition.

In particular embodiments, the blender 32 includes a mixing chamber which will typically comprise a small vessel or a section of pipe. In such cases, the vessel or pipe may be provided with mixing means, such as baffles, adapted to promote turbulence and rapid homogenisation of the individual components.

In certain embodiments of the invention, the blender 32 includes means for controlling the blending of two or more streams to achieve a desirable optimised substrate stream 33. For example, the blender 32 may include means to control the flow rates of each of the streams 1 and 31 entering the blender 32 such that a desirable composition of stream 33 is achieved (e.g. desirable CO:H2 ratio). The blender also preferably includes monitoring means (continuous or otherwise) downstream of the mixing chamber. In particular embodiments, the blender includes a processor adapted to control the flow rates and/or compositions of the various streams as a result of feedback from the monitoring means.

EXAMPLES

The invention will now be further described in more detail with reference to the following non-limiting examples.

The media and solutions used in the fermentations described in these examples contains the following components, unless otherwise noted.

Media:

TABLE 1 composition of media LM23 and LM33

| Media Component | Concentration per 1.0 L of Media (LM23) | Concentration per 1.0 L of Media (LM33) |
|---|---|---|
| MgCl$_2$•6H$_2$O | 0.5 g | 0.5 g |
| NaCl | 0.2 g | 0.2 g |
| CaCl$_2$ | 0.2 g | 0.2 g |
| 100 mM sodium phosphate buffer (pH 6.0)* | 160 ml | — |
| NaH$_2$PO$_4$ | — | 2.04 g |
| NH$_4$Cl | 0.6 g | 2.5 g |
| 85% H$_3$PO$_4$ | 0.05 ml | — |
| KCl | 0.15 g | 0.15 g |
| Composite trace metal solution (LSO6) | 10 mL | 10 mL |
| Composite B vitamin Solution (LS03) | 10 mL | 10 mL |
| Resazurin (1000 mg/L stock) | 1 mL | 2 mL |
| FeCl$_3$ | 0.0025 g | 0.01 g |
| Cysteine HCl monohydrate | 0.75 g | 0.5 g |
| Agarose (optional) | 15 g | 15 g |
| Distilled water | To 1 litre | To 1 litre |

*Combine NaH$_2$PO$_4$ (13.2 g) and Na$_2$HPO$_2$•7H$_2$O (1.1 g) in H$_2$O (1 L).

TABLE 2

Composition of vitamin solution (LS03) and trace metal solution (LS06)

| Composite B vitamin Solution (LS03) | per L of Stock | Composite trace metal solution (LSO6) | per L of stock |
|---|---|---|---|
| Biotin | 20.0 mg | Nitrilotriacetic Acid | 1.5 g |
| Folic acid | 20.0 mg | MgSO$_4$•7H$_2$O | 3.0 g |
| Pyridoxine hydrochloride | 10.0 mg | MnSO$_4$•H$_2$O | 0.5 g |
| Thiamine•HCl | 50.0 mg | NaCl | 1.0 g |
| Riboflavin | 50.0 mg | FeSO$_4$•7H$_2$O | 0.1 g |
| Nicotinic acid | 50.0 mg | Fe(SO$_4$)$_2$(NH$_4$)$_2$•6H$_2$O | 0.8 g |
| Calcium D-(*)-pantothenate | 50.0 mg | CoCl$_2$•6H$_2$O | 0.2 g |
| Vitamin B12 | 50.0 mg | ZnSO$_4$•7H$_2$O | 0.2 g |
| p-Aminobenzoic acid | 50.0 mg | CuCl$_2$•2H$_2$O | 0.02 g |

TABLE 2-continued

Composition of vitamin solution (LS03) and trace metal solution (LS06)

| Composite B vitamin Solution (LS03) | per L of Stock | Composite trace metal solution (LSO6) | per L of stock |
|---|---|---|---|
| Thioctic acid | 50.0 mg | AlK(SO$_4$)$_2$•12H$_2$O | 0.02 g |
| Distilled water | To 1 Litre | H$_3$BO$_3$ | 0.30 g |
| | | NaMoO$_4$•2H$_2$O | 0.03 g |
| | | Na$_2$SeO$_3$ | 0.02 g |
| | | NiCl$_2$•6H$_2$O | 0.02 g |
| | | Na$_2$WO$_4$•6H$_2$O | 0.02 g |
| | | Distilled water | To 1 Litre |

Methodology

Media

Media solutions LM23 and LM33 were prepared at pH 5.5 as follows. All ingredients with the exception of cysteine HCL were mixed in 400 ml dH2O. This solution was made anaerobic by heating to boiling and allowing it to cool to room temperature under a constant flow of 95% CO$_3$ 5% CO2 gas. Once cool, the cysteine HCL was added and the pH of the solution adjusted to 5.5 before making the volume up to 1000 ml (for example 1) or 500 mL (for example 2). Anaerobicity was maintained throughout the experiments.

Steel Mill Off Gas

Steel mill off gas was obtained from the New Zealand Steel Glenbrook facility in Glenbrook, New Zealand. More particularly, it was captured and stored in gas impermeable bags or pressurised in steel gas cylinders at 100-130 bar. Steel mill off gases stored within the bags were accessed via a gas impermeable butyl rubber septa. The steel mill off gas composition varies over time depending on the stage of steel production. However, the gas was collected during the decarburisation process and such gases typically contain CO: 43-50%; CO2: 17-20%; H2: 2-3%; N2: 27-34%.

Steel Mill Scrubber Water

Water, used to scrub (cleanse) the KOBM off-gas stream at the New Zealand Steel Glenbrook facility in Glenbrook, New Zealand, was filtered once using a Buchner funnel and vacuum line through S95 filter paper. The pH of the filtered water was adjusted to 5.5 and 95% CO$_3$ 5% CO2 gas was bubbled through for 45 minutes prior to further use.

Bacteria

*Clostridium autoethanogenum* were obtained from the German Resource Centre for Biological Material (DSMZ). The accession number given to the bacteria is DSMZ 10061. Alternatively, the *Clostridium autoethanogenum* used is that deposited at the German Resource Centre for Biological Material (DSMZ) and allocated the accession number 19630.

Sampling and Analytical Procedures

Media samples were taken at intervals over a 5 day period. Each time the media was sampled care was taken to ensure that no gas was allowed to enter into or escape from the reactors/serum bottles.

All samples were used to establish the absorbancy at 600 nm (spectrophotometer) to determine cell density and the level of substrates and products were determined by HPLC and GC. HPLC was routinely used to quantify the level of acetate, ethanol. GC was used to quantify the percentage of gas (v/v) of carbon monoxide, carbon dioxide, hydrogen and nitrogen.

HPLC

HPLC System Agilent 1100 Series. Mobile Phase: 0.0025N Sulphuric Acid. Flow and pressure: 0.800 mL/min. Column: Alltech IOA; Catalog #9648, 150×6.5 mm, particle size 5 µm. Temperature of column: 60° C. Detector: Refractive Index. Temperature of detector: 45° C.

Method for sample preparation: 400 µL of sample+50 µL of 0.15M ZnSO$_4$+50 µL of 0.15M Ba(OH)$_2$ into an eppendorf tube. Centrifuge 10 min at 12,000 rpm, 4° C. Transfer 200 µL supernatant into an HPLC vial and inject into the HPLC instrument 5 µL.

Gas Chromatography

A Gas Chromatograph CP-4900 Micro-GC, dual channel was used: CP-4900 channel Molecular Sieve 5A PLOT, 10 m, 0.25 mm ID, 4.2 seconds backflush, 70 C. injector and column temperature, Argon carrier gas 200 kPa, 40 millisecond injection. CP-4900 channel PoraPLOT Q 10 m, 0.25 mm ID, 70 C. injector temperature and 90 C. column temperature, Helium carrier gas 150 kPa, 40 millisecond injection. 20 seconds sampling time. 2 minutes method run time. The sample line was heated to 70 C. and linked with a Nafion dryer.

Example 1

Fermentation Using Steel Mill Off Gas

Example 1a

Serum Bottle

Incubation was performed in 250 ml sealed serum bottles each containing 50 ml of the media. The headspace of each serum bottle was first flushed three times with CO2, before being evacuated and filed with the collected steel mill off gas to a final pressure of 25 psig. Each bottle was inoculated with 1 ml of a *Clostridium autoethanogenum* culture. A shaking incubator was used and the reaction temperature was maintained at 37° C.

Media samples were taken at intervals over a 15 day period. Each time the media was sampled. Care was taken to ensure that no gas was allowed to enter into or escape from the serum bottle.

All samples were used to establish the cell density and the level of acetate.

Figure 14:
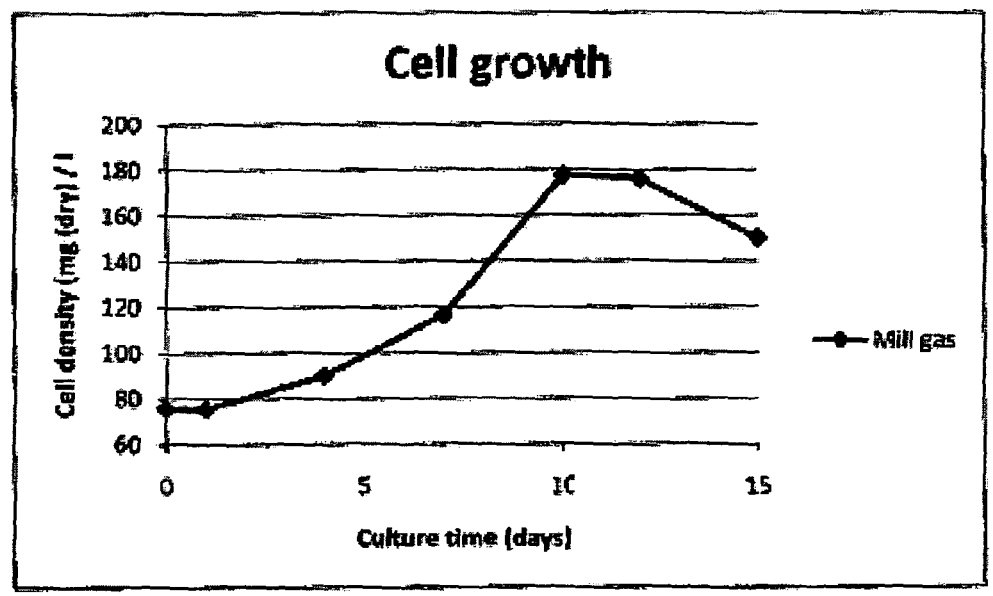
FIG. 14: illustrates microbial growth with time when steel mill gases are used as a resource.
Figure 15:
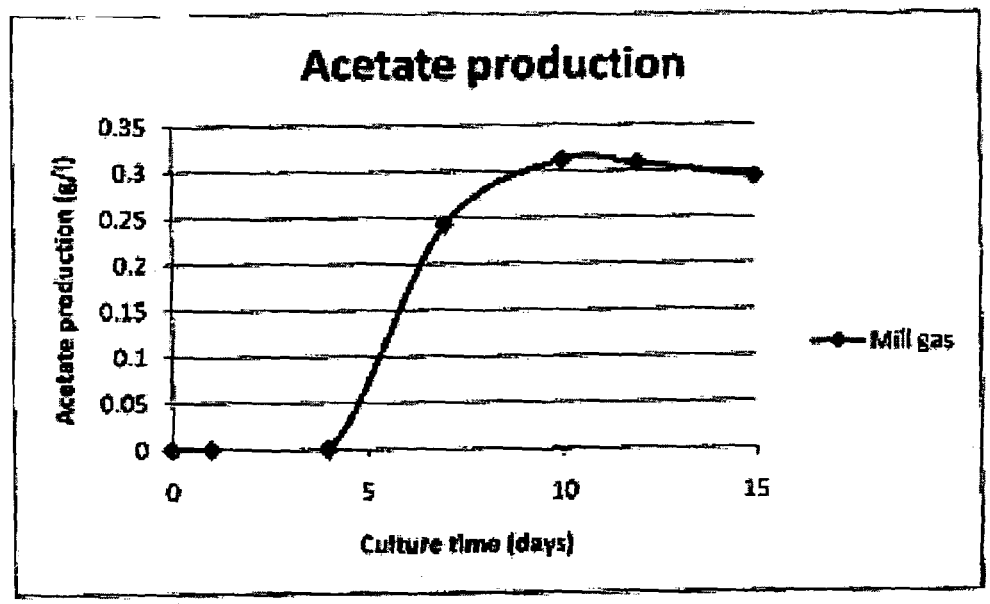
FIG. 15: illustrates product synthesis, namely acetate production, with time when steel mill gases are used as a resource.

As can be seen from FIGS. 14 and 15, cell growth and acetate production rose during the first 10 days before subsequently slowly tailing off. Thus, cell growth and acetate production were readily supported using the steel mill off gas even though no additional treatment steps were performed on the gas prior to its use in the fermentation reaction.

Example 1b

Serum Bottle

Incubation was performed in 234 ml sealed serum bottles each containing 50 ml of the media LM33. The 184 ml headspace of each serum bottle was first flushed three times with steel mill off gas, before being evacuated and filled to an overpressure of 30 psig. Each bottle was inoculated with 2 ml of a *Clostridium autoethanogenum* culture. A shaking incubator was used and the reaction temperature was maintained at 37° C. The results of the experiments are provided in Table 3.

TABLE 3

Serum bottle (30psig; 50% CO; 18% CO2; 3% H2; 29% N2)

|  | Day 0 | Day 1 | Day 2 |
|---|---|---|---|
| Biomass (g/L) | 0.08 | 0.22 | 0.19 |
| Acetate (g/L) | 0.4 | 1.4 | 3.2 |
| Ethanol (g/L) | 0 | 0 | 0.3 |
| Overpressure (psig) | 30 | 28 | 18 |

Example 1c

10 L Continuous Stirred Tank Reactor

A Bioflo 3000 bioreactor was filled with 5 L of the media LM33 without Cysteine nor vitamins solution (LS03) and autoclaved for 30 minutes at 121° C. While cooling down, the media was sparged with N2 and the LS03 solution as well as Cysteine was added. The gas was switched to steel mill off gas prior to inoculation with 150 ml of a *Clostridium autoethanogenum* culture. The bioreactor was maintained at 37° C. and stirred at 200 rpm at the start of the culture with a gas flow of 60 ml/min. During the growth phase, the agitation was increased to 400 rpm and the gas flow was set to 100 ml/min. The pH was set to 5.5 and maintained by automatic addition of 5 M NaOH. The results of this experiment, including gas consumption are provided in Table 4.

TABLE 4

CSTR fermentation supplied with steel mill gas

|  | Day 1 | Day 2 | Day 3 | Day 4 | Day 5 |
|---|---|---|---|---|---|
| Biomass (g/L) | 0.05 | 0.08 | 0.30 | 0.28 | 0.20 |
| Acetate (g/L) | 0.40 | 0.78 | 2.76 | 3.10 | 4.03 |
| Ethanol (g/L) | 0.00 | 0.00 | 0.00 | 0.48 | 0.71 |
| Gas Flow in (mL/min) | 60 | 60 | 100 | 100 | 100 |
| CO [%] gas in | 49.5 | 49.5 | 49.5 | 49.5 | 49.5 |
| CO2 [%] gas in | 17.5 | 17.5 | 17.5 | 17.5 | 17.5 |
| H2 [%] gas in | 2.9 | 2.9 | 2.9 | 2.9 | 2.9 |
| N2 [%] gas in | 27.7 | 27.7 | 27.7 | 27.7 | 27.7 |
| Gas flow out (mL/min) | 55 | 55 | 73 | 94 | 92 |
| CO [%] gas out | 49.2 | 35.8 | 16.4 | 46.1 | 45.5 |
| CO2 [%] gas out | 16.9 | 30.6 | 44.6 | 21.1 | 21.1 |
| H2 [%] gas out | 3.2 | 3.2 | 1.1 | 3.2 | 3.2 |
| N2 [%] gas out | 30.4 | 30.4 | 37.8 | 29.5 | 30.2 |

Example 1d

50 L Gas Lift Reactor

A 50 L gas-lift reactor (2900 mm height×150 mm diameter and draft tube 2000 mm height×95 mm diameter) was filled with 37 L of the media LM33 filter sterilised through a 0.2 micrometer pore filter (Pall KA2 DFL P2 filter). The media was sparged for 18 h with nitrogen before switched to steel mill off gas prior to inoculation with 5 L of a *Clostridium autoethanogenum* culture. The gas-lift reactor was maintained at 37° C. and mixing was achieved by recirculating the headspace gas at 15 L/min. The Gas flow into the reactor was 500 ml/min at the start. The headspace overpressure was maintained at 8 psig. During the growth phase, the gas flow into the reactor was increased to 1000 ml/min. The pH was set to 5.5 and maintained by automatic addition of 5 M NaOH. The results of this experiment, including gas consumption are provided in Table 5.

TABLE 5

Gas-Lift reactor fermentation supplied with steel mill gas

|  | Day 1 | Day 2 | Day 3 | Day 4 | Day 5 |
|---|---|---|---|---|---|
| Biomass (g/L) | 0.15 | — | — | 0.36 | 0.36 |
| Acetate (g/L) | 0.87 | 3.93 | 7.90 | 9.44 | 10.86 |
| Ethanol (g/L) | 0.00 | 0.00 | 0.21 | 0.38 | 0.48 |
| Gas Flow in (mL/min) | 500 | 500 | 1000 | 1000 | 1000 |
| CO [%] gas in | 43.6 | 43.6 | 43.6 | 44.3 | 44.3 |
| CO2 [%] gas in | 19.7 | 19.7 | 19.7 | 20.0 | 20.0 |
| H2 [%] gas in | 2.8 | 2.8 | 2.8 | 2.8 | 2.8 |
| N2 [%] gas in | 33.9 | 33.9 | 33.9 | 32.8 | 32.8 |
| Gas flow out (mL/min) | 341 | — | — | 690 | 716 |
| CO [%] gas out | 29.1 | — | — | 33.1 | 41.3 |
| CO2 [%] gas out | 29.5 | — | — | 28.5 | 22.7 |
| H2 [%] gas out | 2.9 | — | — | 3.0 | 2.6 |
| N2 [%] gas out | 38.4 | — | — | 34.8 | 33.5 |

Particular embodiments of the invention increase the applicability of microbial fermentation reactions using industrial off gases, particularly for the production of ethanol by *Clostridium autoethanogenum*. Waste gases comprising CO obtained directly from industrial processes can be used as a substrate in fermentation reactions to produce products such as acetate and/or ethanol. This will result in capturing carbon in waste gases thus ameliorating or reducing waste produced by industrial processes, particularly steel manufacture, and lowering the costs associated with operating fermentation reactions.

Example 2

Fermentation Using Scrubber Water

Under a continuous gas flow of 95% $CO_3$ 5% CO2, 25 ml of LM23 media was dispensed into 250 ml serum bottles and mixed with either 25 ml of dH2O (control bottles) or 25 ml of pH adjusted anaerobic scrubber water (experimental bottles). All bottles were stopped with gas impermeable butyl rubber septa and crimp sealed before autoclaving at 121° C. for 20 minutes.

Once cool, all serum bottles were inoculated with 1 ml of a *Clostridium autoethanogenum* culture that was actively growing on 95% CO, 5% CO2. Headspace gas was pressurised to 35 psig with 95% CO, 5% CO2. An initial media sample was taken aseptically from each bottle. Bottles were placed on a shaking incubator at 37° C.

Media samples were taken at regular intervals over a 15 day period. Each time the media was sampled the headspace of each bottle was flushed three times with 95% CO, 5% CO2 gas before pressurising with this gas to 35 psig.

All samples were used to establish the cell concentration plus the level of ethanol and acetate in each culture.

Results

Figure 16:
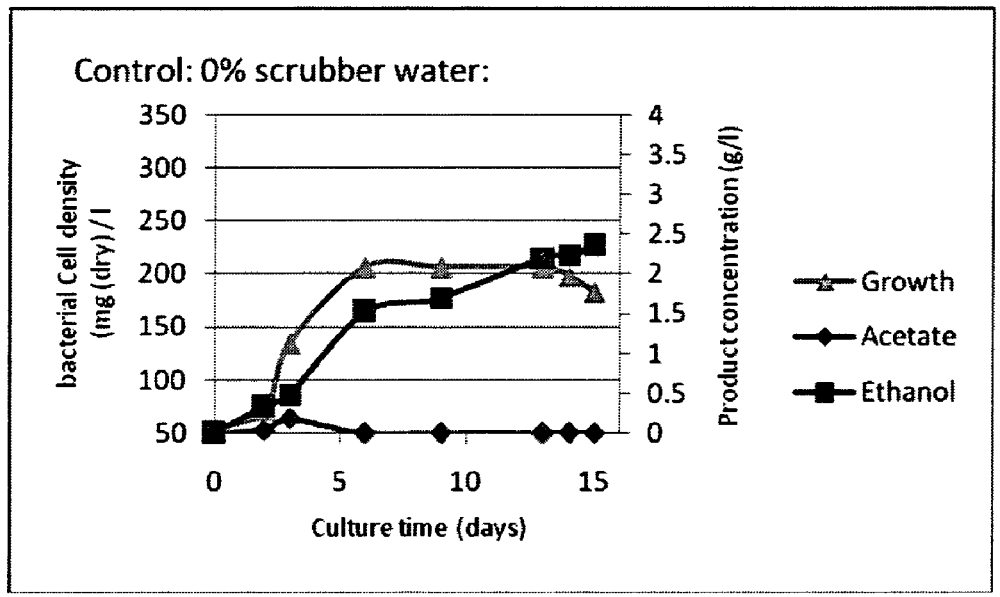
FIG. 16: illustrates bacterial growth and product synthesis with time in laboratory media; and, FIG. 17: illustrates bacterial growth and product synthesis with time using laboratory media mixed with steel mill scrubber water in a ratio of 1:1.
Figure 17:
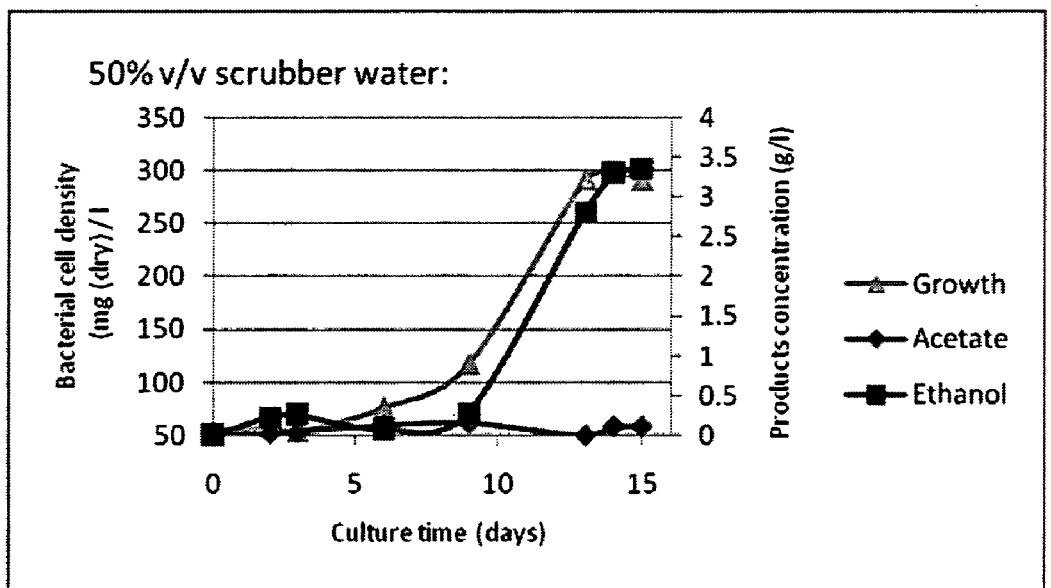

As can be seen from FIGS. 16 and 17, the impact of adding 50% scrubber water to the media included:
1. Lower levels of acetate production;
2. 45% increase in final bacterial density; and
3. 44% increase in ethanol production level As such, particular embodiments of the invention increase the efficiency of growth and alcohol production in fermentation reactions, particularly production of ethanol by *Clostridium autoethanogenum*. Waste material from industrial processes can be used to supplement the nutrient media used in fermentation reactions. In particular, scrubber water can be used as an alternative primary feedstock or substrate for microbial fermentation reactions. This will result in amelioration or reduction of waste produced by industrial processes, particularly steel manufacture, reduction of the level of media required to support fermentation reactions, and reduction of the level of acetate by-product in production of ethanol by fermentation, thus improving overall efficiency of fermentation reactions and lowering the costs associated with operating such reactions.

The invention has been described herein with reference to certain preferred embodiments, in order to enable the reader to practice the invention without undue experimentation. Those skilled in the art will appreciate that the invention can be practiced in a large number of variations and modifications other than those specifically described. It is to be understood that the invention includes all such variations and modifications. Furthermore, titles, headings, or the like are provided to aid the reader's comprehension of this document, and should not be read as limiting the scope of the present invention. The entire disclosures of all applications, patents and publications cited herein are herein incorporated by reference.

More particularly, as will be appreciated by one of skill in the art, implementations of embodiments of the invention may include one or more additional elements. Only those elements necessary to understand the invention in its various aspects may have been shown in a particular example or in the description. However, the scope of the invention is not limited to the embodiments described and includes systems and/or methods including one or more additional steps and/or one or more substituted steps, and/or systems and/or methods omitting one or more steps.

The reference to any prior art in this specification is not, and should not be taken as, an acknowledgement or any form of suggestion that that prior art forms part of the common general knowledge in the field of endeavour in any country.

Throughout this specification and any claims which follow, unless the context requires otherwise, the words "comprise", "comprising" and the like, are to be construed in an inclusive sense as opposed to an exclusive sense, that is to say, in the sense of "including, but not limited to".

What we claim is:

1. A method of producing one or more products by microbial fermentation of an industrial process waste gas stream(s), the method comprising:
   i. passing an intermittent waste gas stream(s) comprising CO from an industrial process to a storage tank;
   ii. passing a substantially continuous waste gas stream(s) from the storage tank to a bioreactor comprising a culture of one or more microorganisms; and
   iii. fermenting the culture in the bioreactor to produce one or more fermentation products and an exhaust stream, said fermentation products comprising alcohols and/or acids.

2. The method of claim 1, wherein the fermentation is carried out by culturing one or more carboxydotrophic bacteria in a liquid nutrient medium.

3. The method of claim 2, wherein the carboxydotrophic bacterium is *Clostridium autoethanogenum* and the fermentation product is ethanol and/or acetate.

4. The method of claim 1 wherein the waste gas stream(s) further comprises $CO_2$ and prior to passing the waste stream(s) to the bioreactor, the waste gas stream(s) is treated to remove at least a portion of the $CO_2$ from the waste gas stream(s) and produce a CO enriched waste gas stream(s).

5. The method of claim 1 wherein the exhaust stream comprises unreacted CO substrate and gaseous by-products comprising $CO_2$ and the exhaust stream is withdrawn from the bioreactor and passed to a separation zone where at least a portion of the $CO_2$ is separated from the exhaust stream to produce a $CO_2$ depleted exhaust stream.

6. The method of claim 5 further comprising taking at least a portion of the $CO_2$ depleted exhaust stream and passing it to the bioreactor.

7. The method of claim 1 further comprising adding to the bioreactor scrubber water obtained from treating a waste gas stream(s) from an industrial process.

* * * * *